(12) United States Patent
Duckett, III

(10) Patent No.: US 12,575,724 B2
(45) Date of Patent: Mar. 17, 2026

(54) SCENE ADAPTIVE ENDOSCOPIC ILLUMINATOR WITH FLUORESCENCE ILLUMINATION

(71) Applicant: KARL STORZ Imaging, Inc., Goleta, CA (US)

(72) Inventor: George E. Duckett, III, Castaic, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 533 days.

(21) Appl. No.: 18/085,419

(22) Filed: Dec. 20, 2022

(65) Prior Publication Data

US 2024/0197157 A1 Jun. 20, 2024

(51) Int. Cl.
*A61B 1/06* (2006.01)
*A61B 1/00* (2006.01)
*A61B 1/07* (2006.01)

(52) U.S. Cl.
CPC ........ *A61B 1/0655* (2022.02); *A61B 1/00117* (2013.01); *A61B 1/0623* (2013.01);
(Continued)

(58) Field of Classification Search
CPC ... A61B 1/0627; A61B 1/0623; A61B 1/0638; A61B 1/0615; A61B 1/0625
See application file for complete search history.

(56) References Cited

U.S. PATENT DOCUMENTS 4,281,931 A * 8/1981 Chikama .............. A61B 1/0615
385/119
5,624,380 A * 4/1997 Takayama ............ A61B 1/0058
600/141
(Continued)

FOREIGN PATENT DOCUMENTS

DE         19936958 A1     3/2001
JP        2016137309 A  *  8/2016
WO       2022150465 A1     7/2022

OTHER PUBLICATIONS

Camara, S., International Search Report, Mar. 12, 2024, pp. 1-12, WIPO, Rijswijk.

*Primary Examiner* — Anh Tuan T Nguyen
*Assistant Examiner* — Jae Woo
(74) *Attorney, Agent, or Firm* — David N. Willalpando; Jacqueline Cohen

(57) ABSTRACT

Endoscopic illuminator devices and methods are provided with an adaptive illumination profile. An endoscopic illuminator includes a first and a third illumination element adapted for coupling first illumination light into a light input of an endoscope for illuminating a central area of a field of view of the endoscope. A second and a fourth illumination element are adapted for coupling second illumination light to the light input for illuminating a peripheral area of the field of view, arranged relative to the first illumination element such that the first illumination light enters the light input at a substantially different angle from the first illumination light, and having an illumination level adjustable separately from that of the first and third illumination element. The second and fourth illumination elements provide imaging light in a different spectral band than the first and third illumination elements.

20 Claims, 12 Drawing Sheets

(52) U.S. Cl.
CPC .......... *A61B 1/0627* (2022.02); *A61B 1/0638*
(2013.01); *A61B 1/07* (2013.01)

(56) References Cited

U.S. PATENT DOCUMENTS

| | | | | |
|---|---|---|---|---|
| 6,211,904 | B1* | 4/2001 | Adair | H01L 25/167 |
| | | | | 257/E25.032 |
| 8,657,738 | B2* | 2/2014 | Kitano | A61B 1/0661 |
| | | | | 600/168 |
| 9,880,380 | B2* | 1/2018 | Daidoji | A61B 1/0655 |
| 2009/0292168 | A1* | 11/2009 | Farr | A61B 1/0684 |
| | | | | 600/109 |
| 2010/0020333 | A1* | 1/2010 | Kunz | G02B 23/2461 |
| | | | | 359/709 |
| 2011/0001811 | A1* | 1/2011 | Imade | A61B 1/0653 |
| | | | | 315/307 |
| 2012/0083656 | A1* | 4/2012 | Kuroda | A61B 1/063 |
| | | | | 600/165 |
| 2012/0123205 | A1* | 5/2012 | Nie | A61B 5/0084 |
| | | | | 600/109 |
| 2013/0121005 | A1* | 5/2013 | Dahmen | A61B 1/0692 |
| | | | | 362/318 |
| 2013/0258081 | A1* | 10/2013 | Akui | A61B 1/0625 |
| | | | | 348/68 |
| 2016/0381273 | A1* | 12/2016 | Honda | H04N 23/76 |
| | | | | 348/69 |
| 2017/0280986 | A1* | 10/2017 | Sekowski | H04N 23/56 |
| 2018/0183981 | A1* | 6/2018 | Talbert | A61B 1/07 |
| 2019/0060013 | A1* | 2/2019 | McDowall | G02B 23/2415 |
| 2019/0328207 | A1* | 10/2019 | Ueda | H04N 23/74 |
| 2020/0096753 | A1* | 3/2020 | Oldham | G02B 26/101 |
| 2022/0287553 | A1* | 9/2022 | Tully | A61B 1/0638 |
| 2023/0084030 | A1* | 3/2023 | Samadani | H04N 23/74 |
| | | | | 348/69 |
| 2024/0115120 | A1* | 4/2024 | Halderman | A61B 1/04 |
| 2024/0197159 | A1* | 6/2024 | Duckett, III | A61B 1/00096 |

* cited by examiner

SCENE ADAPTIVE ENDOSCOPIC ILLUMINATOR WITH FLUORESCENCE ILLUMINATION

TECHNICAL FIELD OF THE INVENTION

The invention relates to light sources or illuminators for endoscopes and other scopes.

BACKGROUND OF THE INVENTION

FIG. 1 illustrates an endoscopic imaging system with an endoscopic illuminator according to the prior art. An endoscope 10 includes an endoscopic shaft member 20 attached to a handle or camera head 30. Light collected by an objective lens at the distal end of the endoscopic shaft 20 is alternatively captured by a, usually distally placed, image sensor within the shaft, or relayed down the length of the shaft via a relay lens system to an image sensor located within the camera head. The distal end of the shaft 20 is inserted into an otherwise inaccessible space, such as body cavity accessed through a small incision. An illumination source 40 produces illumination light that is directed into a light guide 50 which carries the illumination light to a light post 60, where the light guide is coupled with another light guide (such as a fiber bundle) that carries the illumination to the distal end of the shaft 20, where it is then able to illuminate a scene within the inaccessible space. As an alternate utilizing an imaging endoscope 10 to provide illumination, an endoscopic light source might simply embody a light pipe comprising a shaft which may be inserted through a separate incision from that of an imaging endoscope.

Current endoscopic illuminators provide illumination with a constant angular profile. Such constant profiles are suboptimal for several reasons. When an endoscope looks down a lumen (a tubular cavity) it is frequently the case that the sides of the lumen, which are close to the endoscope, are over-illuminated while the center of the scene is under-illuminated. Conversely, while looking at a flat or convex scene, it is often the case that the edges of the image are under-illuminated while the center is over-illuminated. A typical endoscopic illuminator does not allow for adjustment in the light source to optimize the spatial illumination.

One solution is to use image processing, either high-dynamic range (HDR) imaging techniques or other localized brightness adjustments techniques, to increase the apparent brightness of dark regions of the detected image. However, such techniques have disadvantages in that that they either reduce resolution, require higher frame rates, or amplify noise in addition to the amplified signal, and require more image processing power.

What is needed are devices and methods to enable improved illumination of endoscopic imaging.

SUMMARY OF THE INVENTION

It is an object of the invention to provide an endoscopic illumination with improved illumination profiles. It is a further object of the invention to provide improved control and controllability of an illumination profile Another object of the invention is to provide such improvements in a manner compatible with various light guides for various endoscopic systems.

According to a first aspect of the invention, an endoscopic illuminator includes first, second, third, and fourth illumination elements. The first illumination element is adapted for coupling first illumination light into a light input of an endoscope for illuminating a central area of a field of view of the endoscope. The second illumination element adapted for coupling second illumination light to the light input for illuminating a peripheral area of the field of view, arranged relative to the first illumination element such that the first illumination light enters the light input at a substantially different angle from the second illumination light, and has an illumination level adjustable separately from that of the first illumination element. The third illumination element is adapted for coupling third illumination light, of a different spectral band than that of the first and second illumination light, into the light input for illuminating the central area. The fourth illumination element is adapted for coupling fourth illumination light, of the same spectral band as the third illumination light, to the light input for illuminating the peripheral area, arranged relative to the third illumination element such that the fourth illumination light enters the light input at a substantially different angle from the third illumination light, and has an illumination level adjustable separately from that of the third illumination element.

According to some implementations of first aspect, the first and second discrete illumination elements provide white light to the endoscopic field of view and the third and fourth discrete illumination elements provide illumination to excite fluorescence in the endoscopic field of view. In some implementations, the third and fourth illumination elements may provide illumination at wavelengths at wavelength between 750 and 800 nm for stimulating Indocyanine green (ICG) or near infrared (NIR) fluorescence.

According to some implementations of first aspect, the illumination elements may each include a light source and a light directing element arranged for directing light from the light source to the light input at their respective different angles.

According to some implementations of first aspect, the light directing elements includes lenses. In some implementations, at least one of the light directing elements includes a parabolic or elliptical mirror. In some implementations, at least one of the light directing elements includes a dichroic beam combiner.

According to some implementations of first aspect, the illumination elements are adapted to couple light into a light input selected from the group comprising: an input of a light post of the endoscope, a light port of the endoscope, an input of a light cable of the endoscope, an input of a light pipe of the endoscope, and an optical element for coupling to a light input for an endoscope.

According to some implementations of first aspect, the endoscopic illuminator also includes a controller coupled to the illumination elements and operable, in a first mode, to automatically adjust the illumination levels of the first and second illumination elements to improve the evenness of illumination over a field of view of the endoscope; and operable, in a second mode, to automatically adjust the illumination levels of the third and fourth illumination elements to improve the evenness of illumination over a field of view of the endoscope. In some implementations, in the first and second modes, the illumination at the edges of the endoscopic field of view is automatically decreased relative to the illumination at the center of the field of view when the endoscope images along a lumen; and the illumination at the edges of the endoscopic field of view is automatically increased relative to the illumination at the center of the field of view when the endoscope images a flat or convex scene.

According to some implementations of first aspect, an optical axis of at least one illumination element providing illumination to the center of the endoscopic field of view is oriented at a slight angle with respect to a longitudinal axis of the light input into which the illumination is coupled.

According to a second aspect of the invention, a method is given for providing illumination for an endoscope. The method includes coupling first illumination light into a proximal end of a light guiding element for an endoscope centered along a first angle relative to the light guiding element. The method also includes illuminating a central area of a field of view of the endoscope from a distal end of the light guiding element with the first illumination light, and while coupling the first illumination light, coupling second illumination light into the light guiding element centered along a second angle substantially different from the first angle. The method also includes illuminating a peripheral area of the field of view with the second illumination light and adjusting an illumination level of the second illumination light relative to that of the first illumination light to improve evenness of illumination in the field of view. The method also includes coupling third illumination light, of a different spectral band than that of the first and second illumination light, into the proximal end of the light guiding element centered along the first angle, and illuminating a central area of a field of view of the endoscope from the distal end of the light guiding element with the third illumination light, and while coupling the third illumination light, coupling fourth illumination light into the light guiding element centered along a substantially different angle than the first angle. The method also includes illuminating a peripheral area of the field of view with the fourth illumination light and adjusting an illumination level of the fourth illumination light relative to that of the third illumination light to improve evenness of illumination in the field of view.

According to some implementations of second aspect, the method also includes detecting a first illumination level in the central area of the field of view, detecting a second illumination level in the peripheral area of the field of view, and, based on the first and second illumination levels, automatically adjusting the illumination level of the third or fourth illumination light.

According to some implementations of second aspect the step of coupling the third illumination light into the proximal end of the light guiding element includes directing the third illumination light at a light guide element which includes a dichroic beam combiner.

According to a third aspect of the invention, an endoscopic imaging system includes an endoscope with a shaft, a light guide extending along at least a portion of the shaft to a distal end of the shaft, and a light input. The system also includes a light source including a first illumination element providing first illumination into the light input, which is emitted by the light guide to illuminate a central area of a field of view of the endoscope. The light source also includes a second illumination element providing second illumination to the light input and arranged relative to the first illumination element such that the second illumination enters the light input at a substantially different angle from the first illumination, which is emitted by the light guide to illuminate a peripheral area of the field of view, the second illumination element having an illumination level adjustable separately from that of the first illumination element. The light source also includes a third illumination element providing third illumination, of a different spectral band than that of the first and second illumination light, into the light input, the third illumination light emitted by the light guide to illuminate a central area of a field of view of the endoscope. Further, the light source includes a fourth illumination element providing fourth illumination of the same spectral band as the third illumination to the light input and arranged relative to the third illumination element such that the fourth illumination enters the light input at a substantially different angle from the third illumination and is emitted by the light guide to illuminate a peripheral area of the field of view, the fourth illumination element having an illumination level adjustable separately from that of the third illumination element.

According to some implementations of the third aspect, the endoscopic imaging system also includes a controller coupled to the first and second illumination elements. The controller is operable in a first mode to adjust at least one of the first and second illumination elements to improve the evenness of illumination over an endoscopic field of view and is operable in a second mode to adjust at least one of the third and fourth illumination elements to improve the evenness of illumination over the endoscopic field of view.

According to some implementations of the third aspect, the first and second discrete illumination elements provide white light to the endoscopic field of view and the third and fourth discrete illumination elements provide illumination to excite fluorescence in the endoscopic field of view. According to some implementations, the third and fourth illumination elements provide illumination at wavelength between 750 and 800 nm for stimulating Indocyanine green (ICG) or near infrared (NIR) fluorescence.

According to some implementations of the third aspect, the third and fourth illumination elements each include a light source and a light directing element arranged for directing the illumination from the light source to the light input at their respective different angles. According to some implementations, at least one of the light directing elements includes a dichroic beam combiner.

These and other features of the invention will be apparent from the following description of the preferred embodiments, considered along with the accompanying drawings.

BRIEF DESCRIPTION OF THE DRAWINGS

The present invention will become more fully understood from the detailed description given herein and the accompanying drawings which are given by way of illustration only, and thus are not limitative of the present invention, and wherein.

DETAILED DESCRIPTION OF EXAMPLE EMBODIMENTS

Figure 1:
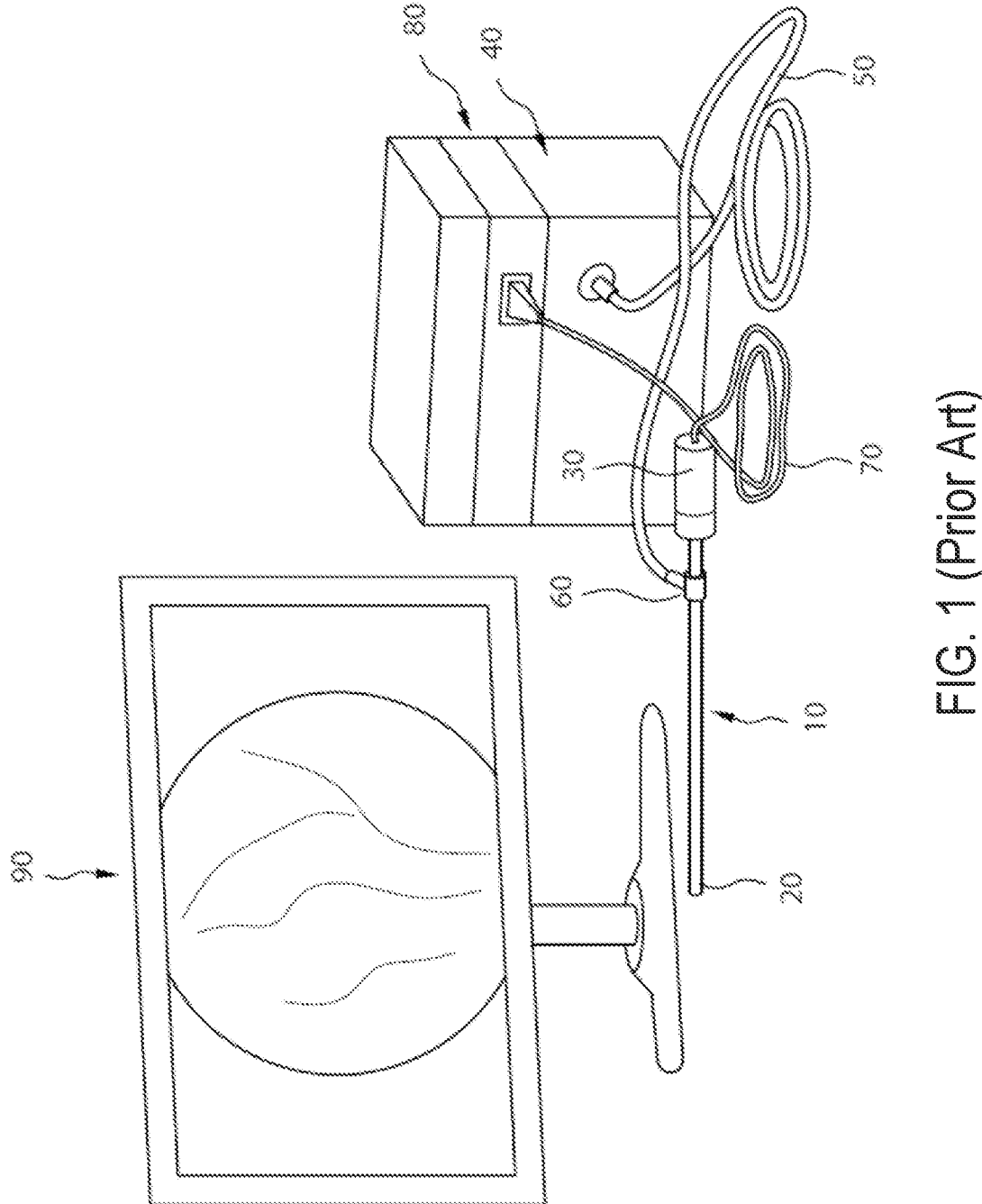
FIG. 1 illustrates a conventional endoscopic imaging system including an endoscope connected by a light guide to an illumination source.
Figure 2:
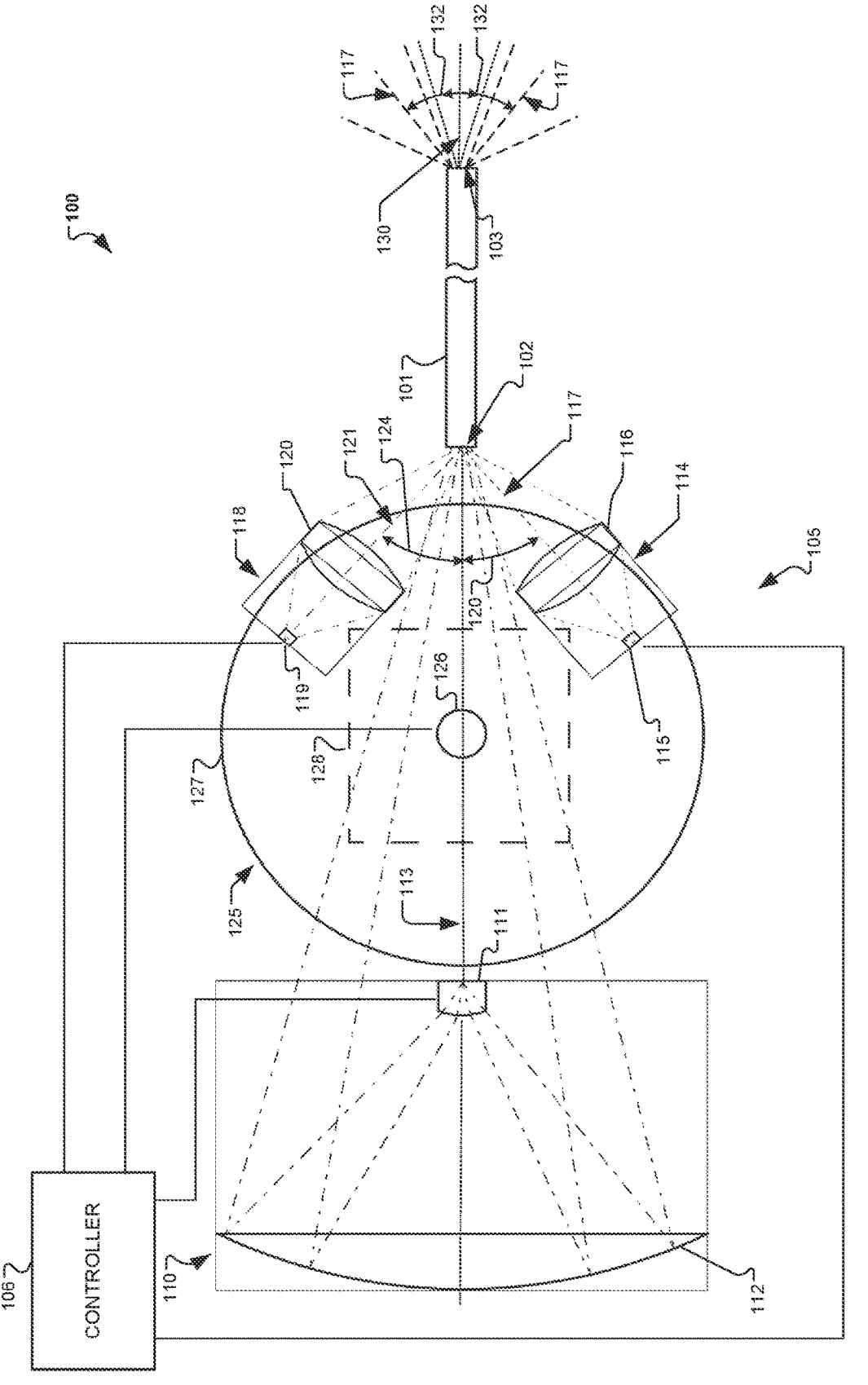
FIG. 2 is a side view diagram depicting a portion of an endoscopic illumination system including an endoscopic illuminator according to some embodiments.
Figure 3:
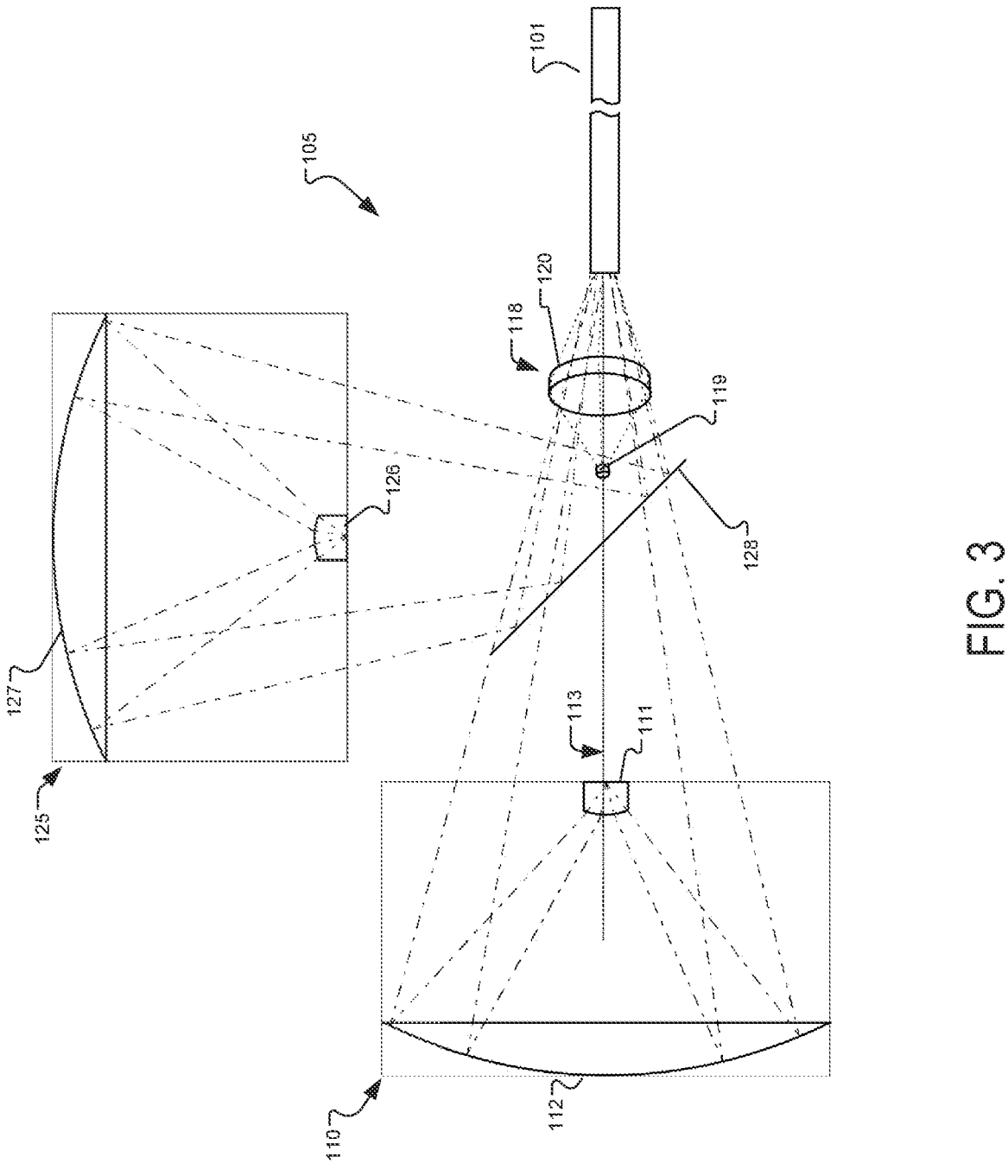
FIG. 3 is a top view diagram of the endoscopic illuminator of FIG. 2.

FIG. 2 is a side view diagram depicting a portion of an endoscopic illumination system 100 including an endoscopic illuminator 105 according to some embodiments. FIG. 3 is a top view diagram of the endoscopic illuminator 105 of FIG. 2. Referring to FIG. 2 and FIG. 3, the depicted portion of endoscopic illumination system 100 generally includes a light guide 101 and an endoscopic illuminator 105 coupled to light guide 101 for providing illumination to a proximal end of light guide 101 at a light input 102. The illumination light is depicted leaving light guide 101 at a distal end 103 for illuminating a field of view of an endoscope or coupling with the internal light guide of an endoscope.

Light guide 101 may be any suitable light guide for an endoscopic system, including a light cable or light pipe, for receiving illumination light and carrying it to the endoscope, where it is typically coupled to a light post. In such embodiments, the light post is optically coupled into a second light guide to carry light to the scope's distal end 103 to illuminate the scope's field of view. Generally, such a light guide includes one or more light carrying members such as fiber optic cables, fiber optic bundles, plastic optical fibers, or glass light pipe elements. In the usual case where the light transmitting components of the light guide maintain a constant diameter over the length of the light guide, the light entering the light guide at light input 102 leaves the light guide at substantially the same angle, with some small amount of dispersion caused by diffraction and the bending of the light fibers. Light input 102 is generally a proximal planar face of light guide 101, such as a proximal face of a fiber optic bundle, fiber optic cable, or other type of light guide. Light guide 101 typically includes an attachment mechanism (not shown) such as a plug or receptacle housing for attaching light guide 101 to light source 105 and positioning light input 102 in a desired position relative to the illumination sources. Light input 102 may embody any suitable light input of a light cable or input of a light pipe of an endoscope. The light cable can then be connected to the light post (as described above) of an endoscope. Alternatively, the light cable (generally removably attached) may be an integral part of the endoscope, obviating the need for a coupling light post. In another embodiment, the endoscopic illuminator may be integrated with the endoscope. Light guide 101 may include more than one light carrying element coupled to each other. For example, a light conditioning element may be positioned in endoscopic illuminator 100 presenting a proximal face to provide light input 102, and a distal face coupled to a light cable for an endoscope or an intervening element.

Endoscopic illuminator 105 includes a housing (not shown), which may be in the form of a light box, a portable light source module, or a portion of a larger control unit for an endoscope in which endoscopic illuminator 105 is integrated. The depicted endoscopic illuminator 105 includes a controller 106, a first illumination element 110, a second illumination element 114, a third illumination element 118, and a fourth illumination element 125.

First illumination element 110 includes a light source 111, a light directing element 112 arranged for collecting light from light source 111 and directing a converging cone of light centered around an angle indicated by line 113 to light input 102 and may include a housing generally indicated by arrow 110. Light directing element 112 is an elliptical mirror in this embodiment, with light source 111 arranged centrally with respect to the elliptical mirror to direct light toward it, which is reflected back toward light input 102.

Second illumination element 114 includes a light source 115, a light directing element 116 optically arranged for collecting light from light source 115 and directing a converging cone of light centered around an angle indicated by line 117 to light input 102 and may include a housing generally indicated by arrow 114. Light sources 111 and 115 are both connected to controller 106 to separately and independently control the illumination level of each light source, as further discussed below. Light sources 111 and 115 may be any suitable light sources which allow for control of the illumination level, such as LEDs, for example, and emit visible light in this embodiment.

Third illumination element 125 includes a light source 126 producing fluorescence excitation light, light directing elements 127 and 128, and may include a housing generally indicated by arrow 125. Light directing elements 127 and 128 optically arranged for collecting light from light source 126 and directing a converging cone of light to light input 102. In this embodiment, light directing element 127 is an elliptical mirror and light directing element 128 is a dichroic beam combiner which passes visible light from illumination element 110 and reflects the fluorescent excitation light from light source 126.

Fourth illumination element 118 includes a light source 119 producing fluorescence excitation light, a light directing element 120 arranged for collecting light from light source 119 and directing a converging cone of light centered around an angle indicated by line 121 to light input 102 and may include a housing generally indicated by arrow 118. Light directing element 120 is a lens positioned between light source 119 and light input 102 to direct light toward light input 102.

Light sources 119 and 126 are both connected to controller 106 to separately and independently control the illumination level of each illumination element, as further discussed below. Light sources 119 and 126 may be any suitable light sources which allow for control of the illumination level, such as LEDs, for example, and emit illumination of a different spectral band than that of the first and second illumination light. For example, in one embodiment, light sources 119 and 126 emit light at wavelengths between 750 and 800 nm for stimulating Indocyanine green (ICG) or other near infrared (NIR) fluorophores.

As depicted, in this embodiment, the angle of line 113 is aligned with a central optical axis of light guide 101 for illuminating a central area of the endoscope's field of view. In other embodiments, the angle of line 113 may be slightly offset from the central optical axis, for example, with an offset of between 0° and 5°. Such an offset, in this and other embodiments described below, offers the benefit of avoiding gaps in the resultant illumination profile. Second illumination element 114 is adapted for coupling second illumination light to light input 102 for illuminating a peripheral area of the field of view, and is optically arranged relative to the first illumination element such that the second illumination light enters the light input at an angle (shown by line 117) substantially different angle from the first illumination light, as shown by the angular arc 120, and has an illumination level adjustable independently from that of the first illumination element 110. Fourth illumination element 118 is adapted for coupling fourth illumination light to light input 102 for illuminating a peripheral area of the field of view, and is optically arranged relative to third illumination element 125 such that the fourth illumination light enters the light input at an angle (shown by line 121) substantially different angle from the third illumination light, as shown by the angular arc 124, and has an illumination level adjustable independently from that of the fourth illumination element 125. In this embodiment, light directing elements 116 and 120 are lenses, but in other embodiments they may include other suitable light directing elements or a combination of elements such as, for example, parabolic or elliptical mirrors, or portions of a larger singular parabolic or elliptical mirror, as further described below.

As shown in FIG. 2, in this embodiment the illumination light from each of the individual illumination elements 110, 114, 118, and 125 is generally not a unidirectional ray but a field of illumination that is focused by light directing elements. The first illumination light leaves its light source 111 as a diverging light field as illustrated by the dotted lines, impinges on light directing elements 112 (here, an elliptical mirror), and is focused toward light input 102 along a central axis indicated by line 113. Preferably, the focal point of light directing element 112 is at or near the surface of light input 102 as depicted by the converging dotted lines on the drawing, providing the benefit that most of the light provided by the illumination element and directed by the directing element will enter the light input 102. A similar arrangement for second illumination element 114 is depicted by the larger dashed lines, with the second illumination light shown as a light field focused by light directing element 116 toward light input 102 along a central axis indicated by lines 117. Illumination elements 118 and 125 have a similar relationship with their corresponding light directing elements and light input 102.

The resulting illumination light emitted at distal end 103 of light guide 101 (which in most implementations will be coupled to the input light post of an endoscope, but which may be an element of an endoscope) is depicted on the right of the diagram. The first illumination light is depicted leaving distal end 103 of light guide 101 to illuminate the central area of the field of view. The central area is generally circular as indicated by the dotted lines at diverging angles around line 130. The second illumination light leaves distal end 103 to illuminate the peripheral area of the endoscope's field of view. Due to the optical properties of light guide 101, while light enters light input 102 at an angle from a single side, exiting light from distal end 103 is generally a ring encircling the central portion of the field of view to illuminate the peripheral portion, with the original field of light being emitted as a ring as indicated by the dashed lines, with a central radius indicated by the lines 117 at angle 132 surrounding the central optical axis of the distal end 103 at the depicted line 130. While the fields of illumination light from illumination elements 110, 114, 118, and 125 are shown as separate, preferably they are configured as two pairs operated in a visible light mode or a fluorescence excitation light mode (110 and 114 for visible light, 118 and 125 for fluorescence excitation light) for which the light field edges overlap to provide a continuous illumination field from the combined illumination. For each pair, this combined illumination field has an adjustable distribution as further discussed below. It should also be noted that some endoscopic systems used in conjunction with the endoscopic illumination system 110 may provide FI excitation illumination and white light illumination simultaneously, and the resultant detected illumination may be conditioned and analyzed separately, as described below with relation to FIG. 12.

In operation, controller 106, coupled to the first illumination element 110 and second illumination element 114, is operable to automatically adjust the illumination levels of the first and second illumination elements 110 and 114 to improve the evenness of illumination over a field of view of the endoscope when in a visible light mode. Controller 106, coupled to the third illumination element 125 and fourth illumination element 118, is operable to automatically adjust the illumination levels of the third and fourth illumination elements 125 and 118 to improve the evenness of illumination over a field of view of the endoscope when in a fluorescence excitation light mode. For example, the illumination at the edges of the endoscopic field of view may be automatically decreased relative to the illumination at the center of the field of view when the endoscope images along a lumen, and automatically increased relative to the illumination at the center of the field of view when the endoscope images a flat or convex scene. While two separate modes are described, the system may alternate between these modes to capture alternate frames of visible and fluorescent light or may operate with both modes simultaneously.

Figure 4:
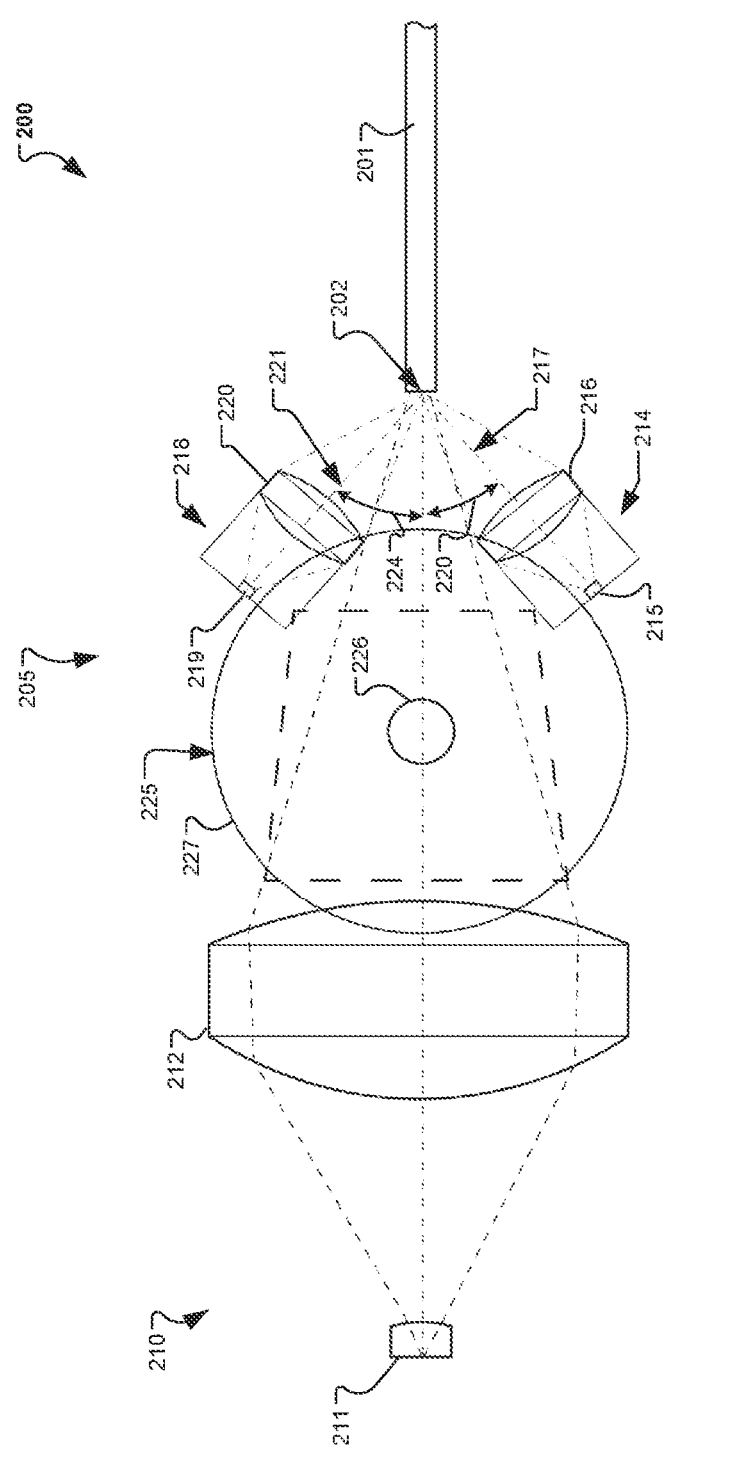
FIG. 4 is a side view diagram depicting a portion of an endoscopic illumination system including an endoscopic illuminator according to some additional embodiments.
Figure 5:
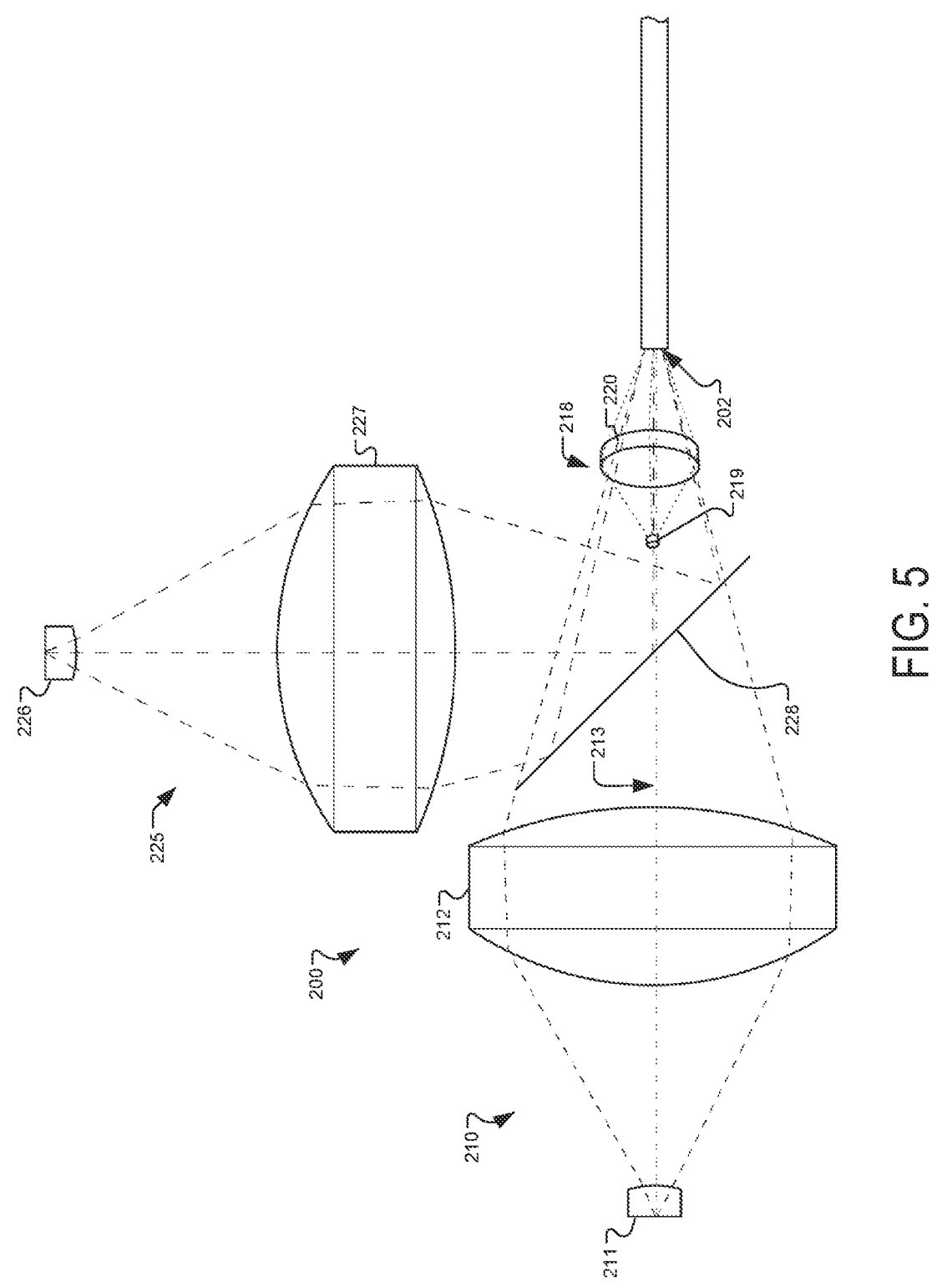
FIG. 5 is a top view diagram of the endoscopic illuminator of FIG. 4.

FIG. 4 is a side view diagram depicting a portion of an endoscopic illumination system 200 including an endoscopic illuminator 205 according to some embodiments. FIG. 5 is a top view diagram of the endoscopic illuminator 205 of FIG. 4. Referring to FIG. 4 and FIG. 5, the depicted portion of endoscopic illumination system 200 generally includes a light guide 201 and an endoscopic illuminator 205 coupled to light guide 201 for providing illumination to a proximal end of light guide 201 at a light input 202. Light guide 201 may be any suitable light guide for an endoscopic system, as described above with respect to light guide 101 of FIG. 2.

Endoscopic illuminator 205 may be embodied in various types of housings as discussed above and includes a controller coupled to the various illumination elements as described above. Endoscopic illuminator 205 generally includes a first illumination element 210, a second illumination element 214, a third illumination element 225, and a fourth illumination element 218.

First illumination element 210 includes a light source 211, a light directing element 212 arranged for collecting light from light source 211 and directing a converging cone of light centered around an angle indicated by line 213 to light input 202 and may include a housing generally indicated by arrow 210. Light directing element 212 is a lens in this embodiment.

Second illumination element 214 includes a light source 215, a light directing element 216 optically arranged for collecting light from light source 215 and directing a converging cone of light centered around an angle indicated by line 217 to light input 202 and may include a housing generally indicated by arrow 214. Light sources 211 and 215 are both connected to a controller to separately and independently control the illumination level of each light source, as further discussed below. Light sources 211 and 215 may be any suitable light sources which allow for control of the illumination level, such as LEDs, for example, and emit visible light in this embodiment.

Third illumination element 225 includes a light source 226 producing fluorescence excitation light, light directing elements 227 and 228 optically arranged for collecting light from light source 226 and directing a converging cone of light to light input 202 and may include a housing generally indicated by arrow 225. In this embodiment, light directing element 227 is a lens and light directing element 228 is a dichroic beam combiner which passes visible light from illumination element 210 and reflects the fluorescent excitation light from light source 226.

Fourth illumination element 218 includes a light source 219 producing fluorescence excitation light, a light directing element 220 arranged for collecting light from light source 219 and directing a converging cone of light centered around an angle indicated by line 221 to light input 202 and may include a housing generally indicated by arrow 218. Light directing element 220 is a lens positioned between light source 219 and light input 202 to direct light toward light input 202.

Light sources 219 and 226 are both connected to a controller to separately and independently control the illumination level of each light source, as further discussed below. Light sources 219 and 226 may be any suitable light sources which allow for control of the illumination level, such as LEDs, for example, and emit illumination of a different spectral band than that of the first and second illumination light. For example, in one embodiment, light sources 219 and 226 emit fluorescence excitation light at wavelengths between 750 and 800 nm for stimulating Indocyanine green (ICG) or other near infrared (NIR) fluorophores.

As depicted, in this embodiment, the angle indicated by line 213 is aligned with a central optical axis of light guide 201 for illuminating a central area of the endoscope's field of view. In other embodiments, the angle may be slightly offset from the central optical axis. Second illumination element 214 is adapted for coupling second illumination light to light input 202 for illuminating a peripheral area of the field of view, and is optically arranged relative to the first illumination element such that the second illumination light enters the light input at an angle (shown by line 217) substantially different angle from the first illumination light, as shown by the angular arc 220, and has an illumination level adjustable independently from that of the first illumination element 210. Fourth illumination element 218 is adapted for coupling fourth illumination light to light input 202 for illuminating a peripheral area of the field of view and is optically arranged relative to third illumination element 225 such that the fourth illumination light enters the light input at an angle (shown by line 221) substantially different angle from the third illumination light, as shown by the angular arc 224. The third illumination element 225 has an illumination level adjustable independently from that of the fourth illumination element 218. In this embodiment, light directing elements 212, 216, 220, and 227 are lenses, but in other embodiments they may include other suitable light directing elements or a combination of elements such as, for example, parabolic or elliptical mirrors, or portions of a larger singular parabolic or elliptical mirror, as further described below.

While FIG. 4 does not depict the distal end of light guide 201, the resulting illumination light emitted at distal end of light guide 201 is similar to that depicted in FIG. 2 and is controlled as described with respect to FIG. 2. While the fields of illumination light from illumination elements 210, 214, 218, and 225 are shown as separate, preferably they are configured as two pairs operated in a visible light mode or a fluorescence excitation light mode (210 and 214 for visible light, 218 and 225 for fluorescence excitation light) for which the illumination light field edges overlap to provide continuous a continuous illumination field from the combined illumination at the distal end of light guide 201. For each pair, this combined illumination field has an adjustable distribution as further discussed below.

Figure 6:
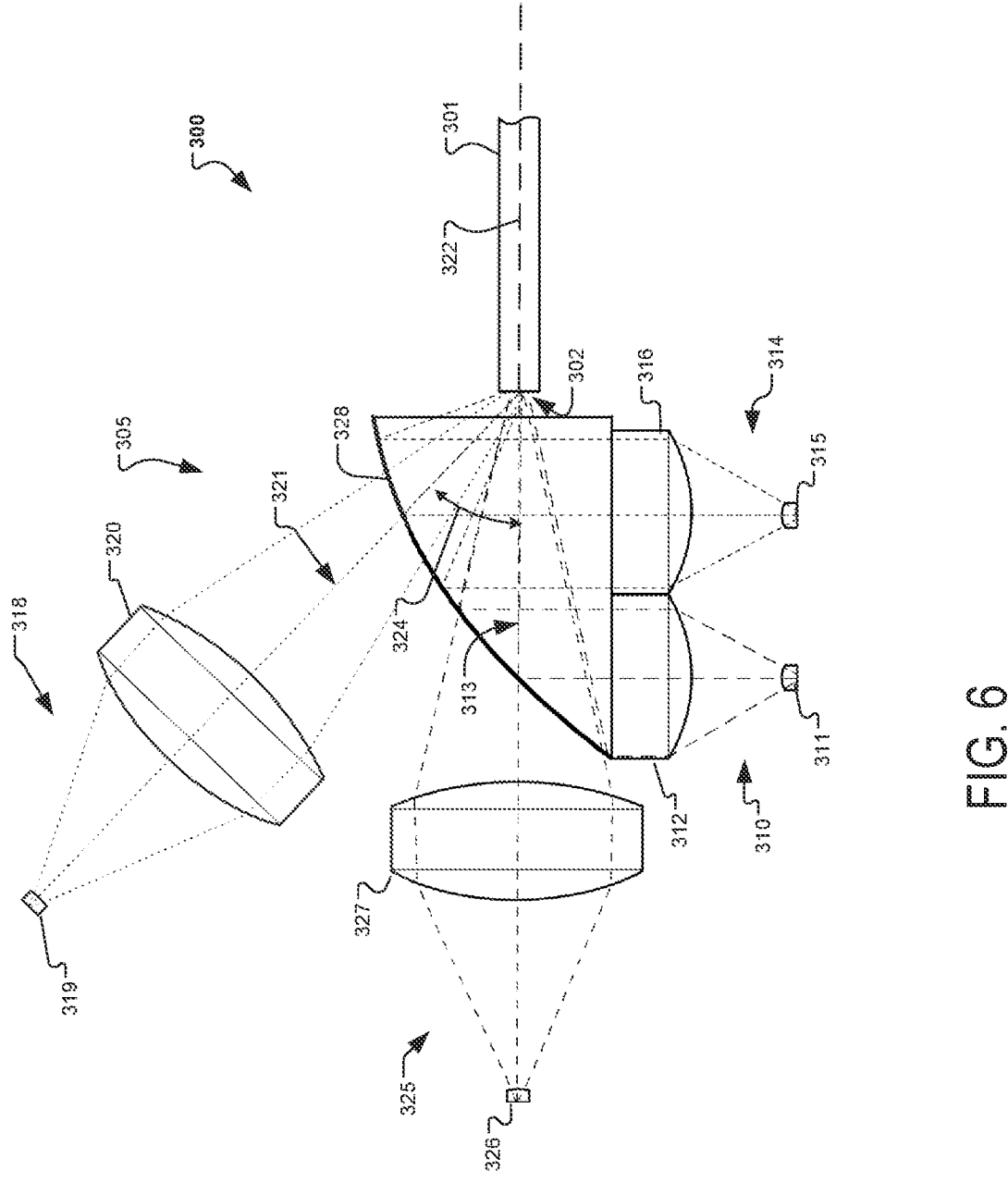
FIG. 6 is a top view diagram depicting a portion of an endoscopic illumination system including an endoscopic illuminator according to some additional embodiments.

FIG. 6 is a top view diagram depicting a portion of an endoscopic illumination system 300 including an endoscopic illuminator 305 according to some embodiments. The depicted portion of endoscopic illumination system 300 generally includes a light guide 301 and an endoscopic illuminator 305 coupled to light guide 301 for providing illumination to a proximal end of light guide 301 at a light input 302. Light guide 301 may be any suitable light guide for an endoscopic system, as described above with respect to light guide 101 of FIG. 2.

Endoscopic illuminator 305 may be embodied in various types of housings as discussed above and includes a controller coupled to the various illumination elements as described above. Endoscopic illuminator 305 generally includes a first illumination element 310, a second illumination element 314, a third illumination element 325, and a fourth illumination element 318.

First illumination element 310 includes a light source 311, a light directing element 312, light directing element 328, and may include a housing generally indicated by arrow 310. Light directing element 312 is a lens arranged for collecting light from light source 311 and directing a parallel field of light toward light directing element 328, which reflects the light into a converging cone centered along an angle indicated by line 313 to light input 302. Light directing element 328 is a parabolically shaped dichroic beam combiner in this embodiment and has a first portion directing light from light source 311 and a second portion directing light from light source 315. Light directing element 328 may be a single mirror or separate mirrors.

Second illumination element 314 includes a light source 315, a light directing element 316, and may include a housing generally indicated by arrow 314. Light directing element 316 is optically arranged for collecting light from light source 315 and directing a parallel field of light toward light directing element 328, which may be shared with light source 311, and reflects the light centered in a converging cone along an angle indicated by line 321 to light input 302. Light sources 311 and 315 are both connected to a controller to separately and independently control the illumination level of each light source, as further discussed below. Light sources 311 and 315 may be any suitable light sources which allow for control of the illumination level, such as LEDs, for example, and emit visible light in this embodiment.

Third illumination element 325 includes a light source 326 producing fluorescence excitation light, a light directing element 327, and may include a housing generally indicated by arrow 325. Light directing element 327 is a lens optically arranged for collecting light from light source 326 and directing a converging cone of light to light input 302, passing through light directing element 328.

Fourth illumination element 318 includes a light source 319 producing fluorescence excitation light, a light directing element 320 arranged for collecting light from light source 319 and directing a converging cone of light centered around an angle indicated by line 321 to light input 302 and may include a housing generally indicated by arrow 318. Light directing element 320 is a lens in this embodiment.

Light sources 319 and 326 are both connected to a controller to separately and independently control the illumination level of each light source, as further discussed below. Light sources 319 and 326 may be any suitable light sources which allow for control of the illumination level, such as LEDs, for example, and emit illumination of a different spectral band than that of the first and second illumination light. For example, in one embodiment, light sources 319 and 326 emit fluorescence excitation light at wavelengths between 750 and 800 nm for stimulating Indocyanine green (ICG) or other near infrared (NIR) fluorophores.

As depicted, in this embodiment, angle 313 is aligned with a central optical axis of light guide 301 for illuminating a central area of the endoscope's field of view. In other embodiments, angle 313 may be slightly offset from the central optical axis, as discussed with relation to the above embodiments. Second illumination element 314 is adapted for coupling second illumination light to light input 302 for illuminating a peripheral area of the field of view, and is optically arranged relative to the first illumination element such that the second illumination light enters the light input at an angle (shown by line 321) substantially different angle from the first illumination light, as shown by the angular arc 324, and has an illumination level adjustable independently from that of the first illumination element 310. Fourth illumination element 318 is adapted for coupling fourth illumination light to light input 302 for illuminating a peripheral area of the field of view and is optically arranged relative to third illumination element 325 such that the fourth illumination light enters the light input at an angle (also shown by line 321) substantially different angle from the third illumination light, as shown by the angular arc 324. The third illumination element 325 has an illumination level adjustable independently from that of the fourth illumination element 318.

While FIG. 6 does not depict the distal end of light guide 301, the resulting illumination light emitted at distal end of light guide 301 is similar to that depicted in FIG. 2 and is controlled as described with respect to FIG. 2. While the fields of illumination light from illumination elements 310, 314, 318, and 325 are shown as separate for illustration purposes, preferably they are configured as two pairs operated in a visible light mode or a fluorescence excitation light mode (310 and 314 for visible light, 318 and 325 for fluorescence excitation light) for which the illumination light field edges overlap to provide a continuous illumination field from the combined illumination at the distal end of light guide 301. For each pair, this combined illumination field has an adjustable distribution as further discussed below.

Figure 7:
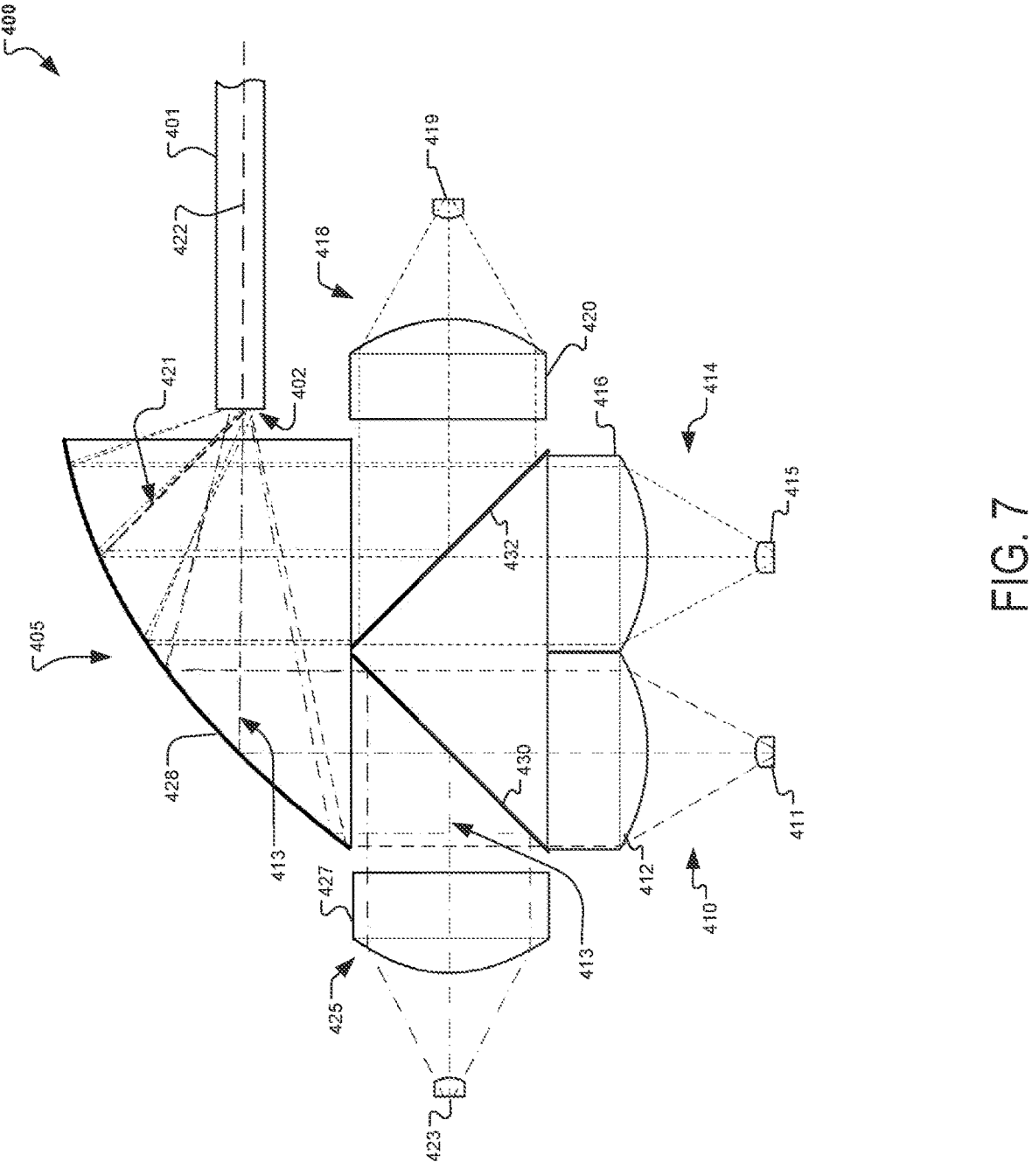
FIG. 7 is a top view diagram depicting a portion of an endoscopic illumination system including an endoscopic illuminator according to additional embodiments.

FIG. 7 is a top view diagram depicting a portion of an endoscopic illumination system 400 including an endoscopic illuminator 405 according to some embodiments. The depicted portion of endoscopic illumination system 400 generally includes a light guide 401 and an endoscopic illuminator 405 coupled to light guide 401 for providing illumination to a proximal end of light guide 401 at a light input 402. Light guide 401 may be any suitable light guide for an endoscopic system, as described above with respect to light guide 101 of FIG. 2.

Endoscopic illuminator 405 may be embodied in various types of housings as discussed above and includes a controller coupled to the various illumination elements as described above. Endoscopic illuminator 405 generally includes a first illumination element 410, a second illumination element 414, a third illumination element 425, and a fourth illumination element 418.

First illumination element 410 includes a light source 411, a light directing element 412, light directing element 428, and may include a housing generally indicated by arrow 410. Light directing element 412 is a lens arranged for collecting light from light source 411 and directing a parallel field of light toward light directing element 428, which reflects the light into a converging cone centered along an angle indicated by line 413 to light input 402. Light directing element 428 is a parabolically shaped mirror in this embodiment and has a first portion directing light from light sources 411 and 425 and a second portion directing light from light sources 415 and 418.

Second illumination element 414 includes a light source 415, a light directing element 416, and may include a housing generally indicated by arrow 414. Light directing element 416 is optically arranged for collecting light from light source 415 and directing a parallel field of light toward light directing element 428, which is shared with light source 411, that reflects the light into a converging cone along an angle indicated by line 421 to light input 402. Light sources 411 and 415 are both connected to a controller to separately and independently control the illumination level of each light source, as further discussed below. Light sources 411 and 415 may be any suitable light sources which allow for control of the illumination level, such as LEDs, for example, and emit visible light in this embodiment.

Third illumination element 425 includes a light source 423 producing fluorescence excitation light, a light directing element 427, a light directing element 430, and may include a housing generally indicated by arrow 425. Light directing element 427 is a lens optically arranged for collecting light from light source 426 and directing a parallel field of light to light directing element 430, which reflects the light toward light directing element 428. Light directing element 430 is a dichroic beam combiner which reflects the fluorescence excitation light wavelengths from light source 423 but passes the visible light wavelengths from light source 411. At light directing element 428, the light from light source 423 is reflected by the curved mirror into a converging cone of light directed at light input 402.

Fourth illumination element 418 includes a light source 419 producing fluorescence excitation light, a light directing element 420, a light directing element 432, and may include a housing generally indicated by arrow 425. Light directing element 420 is a lens optically arranged for collecting light from light source 419 and directing a parallel field of light to light directing element 432, which reflects the light toward light directing element 428. Light directing element 432 is a dichroic beam combiner which reflects the fluorescence excitation light wavelengths from light source 419 but passes the visible light wavelengths from light source 415. At light directing element 428, the light from light source 419 is reflected by the curved mirror into a converging cone of light directed at light input 402. Light sources 419 and 426 are both connected to a controller to separately and independently control the illumination level of each light source, as further discussed below. Light sources 419 and 426 may be any suitable light sources which allow for control of the illumination level, such as LEDs, for example, and emit illumination of a different spectral band than that of the first and second illumination light. For example, in one embodiment, light sources 419 and 423 emit fluorescence excitation light at wavelengths between 750 and 800 nm for stimulating Indocyanine green (ICG) or other near infrared (NIR) fluorophores.

As depicted, in this embodiment, the angle of line 413 is aligned with a central optical axis of light guide 401 for illuminating a central area of the endoscope's field of view. In other embodiments, angle 413 may be slightly offset from the central optical axis, the reason for and benefits of discussed above. Second illumination element 414 is adapted for coupling second illumination light to light input 402 for illuminating a peripheral area of the field of view and is optically arranged relative to the first illumination element such that the second illumination light enters the light input at an angle (shown by line 421) substantially different angle from the first illumination light and has an illumination level adjustable independently from that of the first illumination element 410. Fourth illumination element 418 is adapted for coupling fourth illumination light to light input 402 for illuminating a peripheral area of the field of view and is optically arranged relative to third illumination element 425 such that the fourth illumination light enters the light input at an angle (also shown by line 421) substantially different angle from the third illumination light. The third illumination element 423 has an illumination level adjustable independently from that of the fourth illumination element 418.

While FIG. 7 does not depict the distal end of light guide 401, the resulting illumination light emitted at distal end of light guide 401 is similar to that depicted in FIG. 2 and is controlled as described with respect to FIG. 2. While the fields of illumination light from illumination elements 410, 414, 418, and 425 are shown as separate for illustration purposes, preferably they are configured as two pairs operated in a visible light mode or a fluorescence excitation light mode (410 and 414 for visible light, 418 and 425 for fluorescence excitation light) for which the illumination light field edges overlap to provide a continuous illumination field from the combined illumination at the distal end of light guide 401. For each pair, this combined illumination field has an adjustable distribution as further discussed below.

Figure 8:
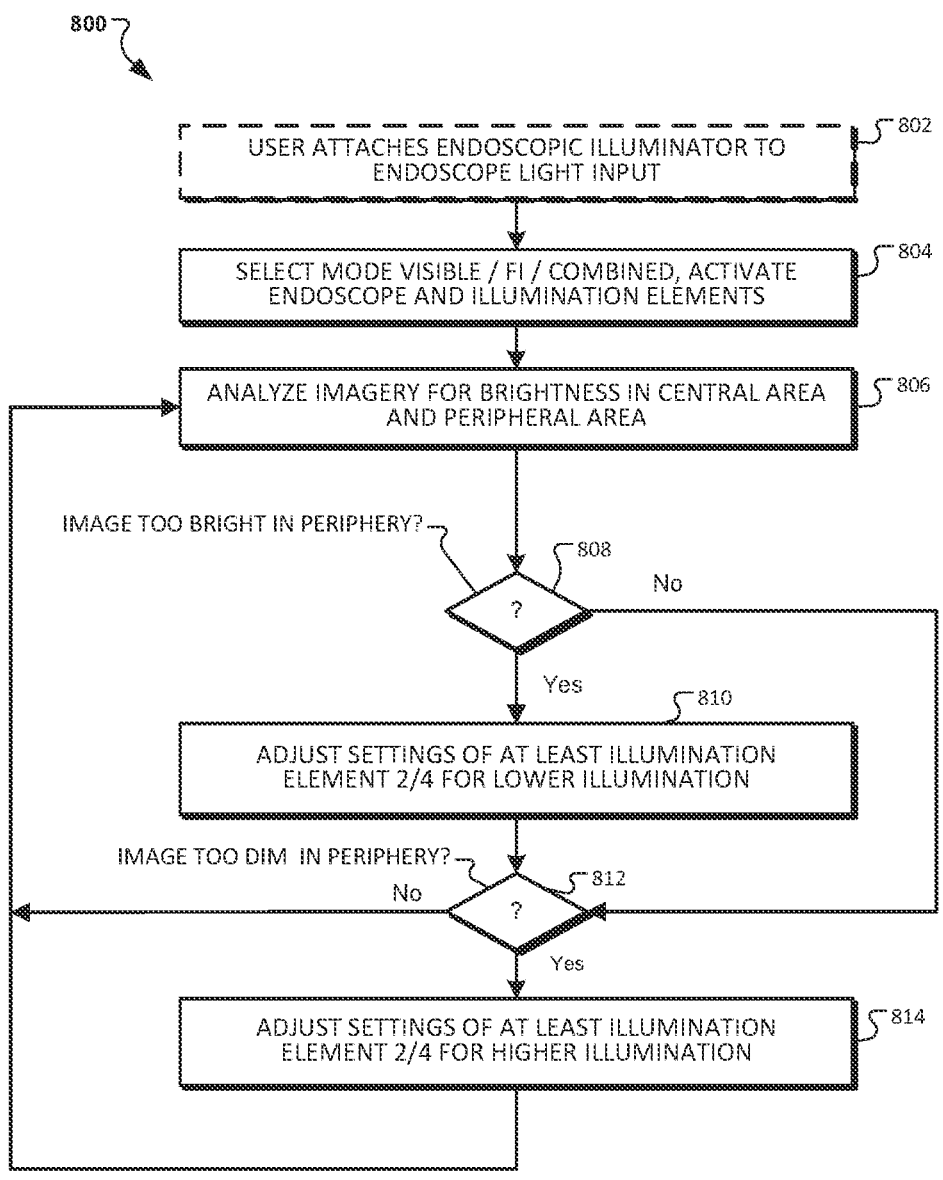
FIG. 8 shows a flowchart of a process for operating an endoscopic illuminator according to some embodiments.

FIG. 8 shows a flowchart 800 of a process for operating an endoscopic illuminator according to some embodiments. The process is suitable for use with all embodiments of an endoscopic illuminator herein and is generally conducted by an electronic controller and control unit coupled to the endoscope. The process may be used in combination with other known illumination control features as, for example, automatic adjustment of overall image brightness. While the process steps are shown in a linear order here, generally they may be conducted in parallel, and may be conducted periodically, continuously, or in an object oriented or event driven control algorithm in which changes in brightness trigger certain control actions. The particular order of steps is therefore not limiting and is shown for illustrative purposes only.

The process starts at block 802 where a user attaches the endoscopic illuminator to the light input of an endoscope. For embodiments in which the endoscopic illuminator is integrated into the endoscope, this step is not used. At block 804, a user activates the endoscope and activates the endoscopic illuminator. The user may also select a mode of operation for the endoscopic illuminator from selections including a visible light imaging mode in which the first and second illumination elements are activated, and a fluorescence imaging mode in which the third and fourth illumination elements are activated. Another mode that may be provided is an alternating mode in which the fluorescence excitation light is provided periodically, and the visible light is provided during alternate periods to produce alternate frames with the two different types of imaging. Yet another mode that may be provided is a combined mode in which both types of light are provided.

As shown at block 806, while the scope is in use, an image processor analyzes imagery from the scope, either the FT imagery or the visible light imagery, or both, depending on the mode. The analysis determines brightness in a central area of the scope field of view, and separately in a peripheral area. At block 808, the process checks if the image is too bright in the periphery. The determination may be made by measuring an overall brightness characteristic in the peripheral area and comparing it against a threshold brightness. Such a condition may exist, for example, if the scope is imaging along a lumen such as a colon (during a colonoscopy) or other tubular cavity, and the second illumination element as described in embodiments above is illuminating at or near the brightness of the first illumination element. In such a case, the walls of the lumen appear in the periphery and are closer to the endoscope tip than the any elements in the central area of the field of view, and so appear brighter. If so, the process goes to block 810 where it automatically adjusts the illumination setting of the second or fourth illumination element, depending on the mode, to reduce illumination, the first or third element to increase illumination to the central area, or adjust both illumination elements accordingly. If the condition is not present at block 808, the process goes to block 812.

At block 812, the process checks whether the imagery is too dim in the periphery. Such a condition may exist, for example, if the scope tip leaves a lumen and enters a larger cavity or changes orientation or position. If not, the process returns to block 806 where it continues to analyze imagery. If so, the process goes to block 814 where it adjusts the settings of the second or fourth illumination element for higher illumination, and then proceeds to block 806. Block 814 may also include adjusting the illumination of first or third illumination element to be lower, depending on its level and the overall image brightness, for example.

The particular implementation of increasing or decreasing illumination at each illumination element may change depending on the type of illumination element used, and may include, for example, increasing or decreasing a pulse-width of a pulse with modulated signal supplying an LED of the illumination element, or increasing or decreasing a voltage or current supplied to the illumination element.

Figure 9:
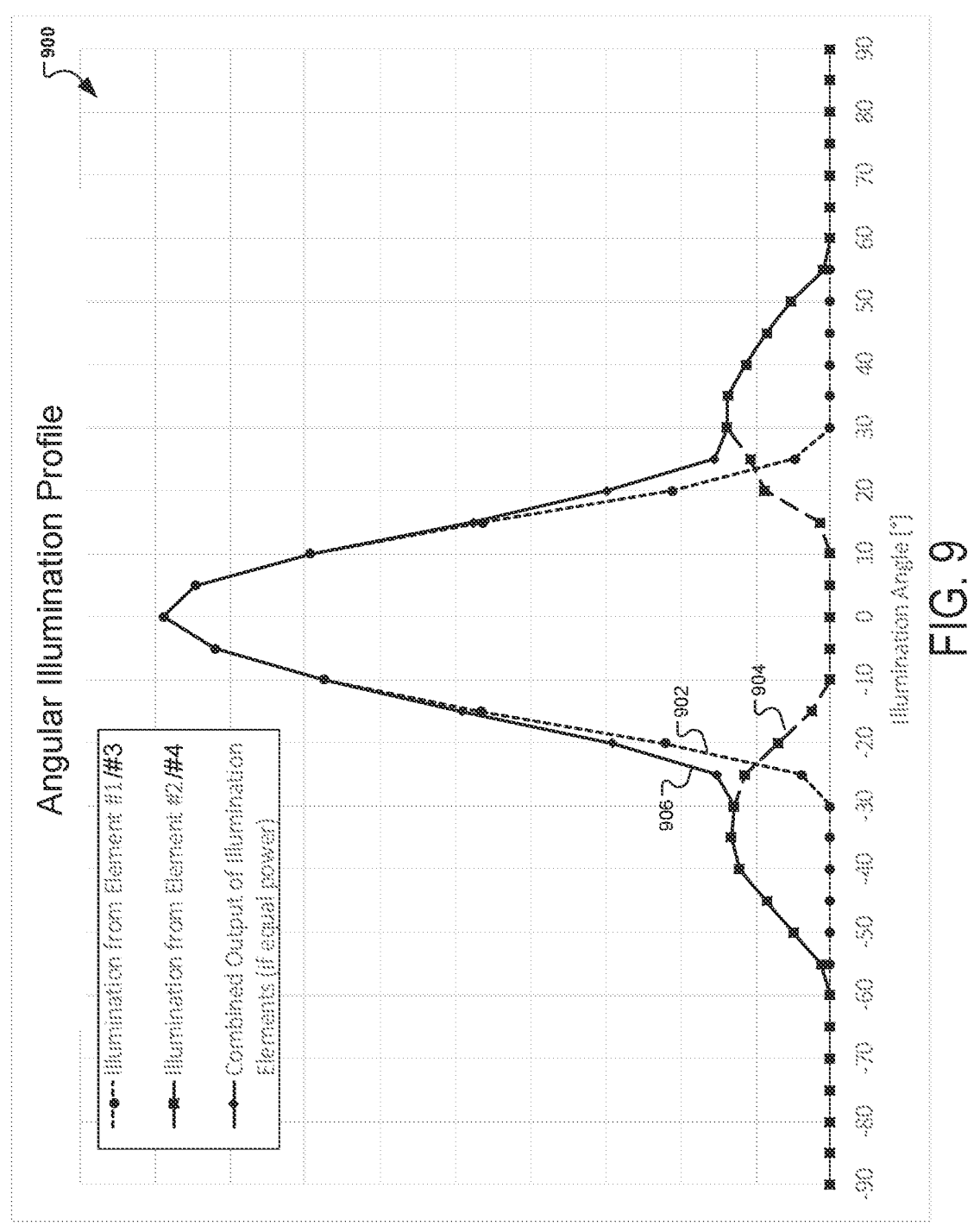
FIG. 9 shows a chart of an angular illumination profile for an endoscopic illuminator according to some embodiments.

FIG. 9 shows a chart 900 of an angular illumination profile for an endoscopic illuminator according to some embodiments, such as the embodiment shown in FIG. 2. The vertical shows the illumination level, and the horizontal axis shows the angle of view as measured from directly perpendicular to the imaging lens or imager at the scope tip.

As can be seen, a first illumination profile 902 shows an angular illumination profile of a first illumination element and third illumination element, which emit light that is then directed, as described above, toward the center of the endoscope field of view. The illumination level or brightness drops off quickly from a peak in the center to a relatively low level at 25 degrees away from the center.

A second illumination profile 904 shows the angular illumination profile of a second illumination element or fourth illumination element as described above. As can be seen, there are two peaks on either side which illustrate the "ring" of light provided toward the image periphery by the second or fourth illumination elements. This profile is low in the center and higher on each side with a peak around 35 degrees in this example.

A third profile 906 shows the combined illumination profile of both illumination elements, depending on the mode the first and second illumination elements together or the third and fourth illumination elements together. The particular illumination levels are shown merely as an example to illustrate the profile and change as the illumination levels are adjusted to change the shape of the overall profile. This profile might be one selected for illumination down a lumen where a lower intensity of light is desired at the peripheral regions and a higher intensity in the center of the image.

Figure 10:
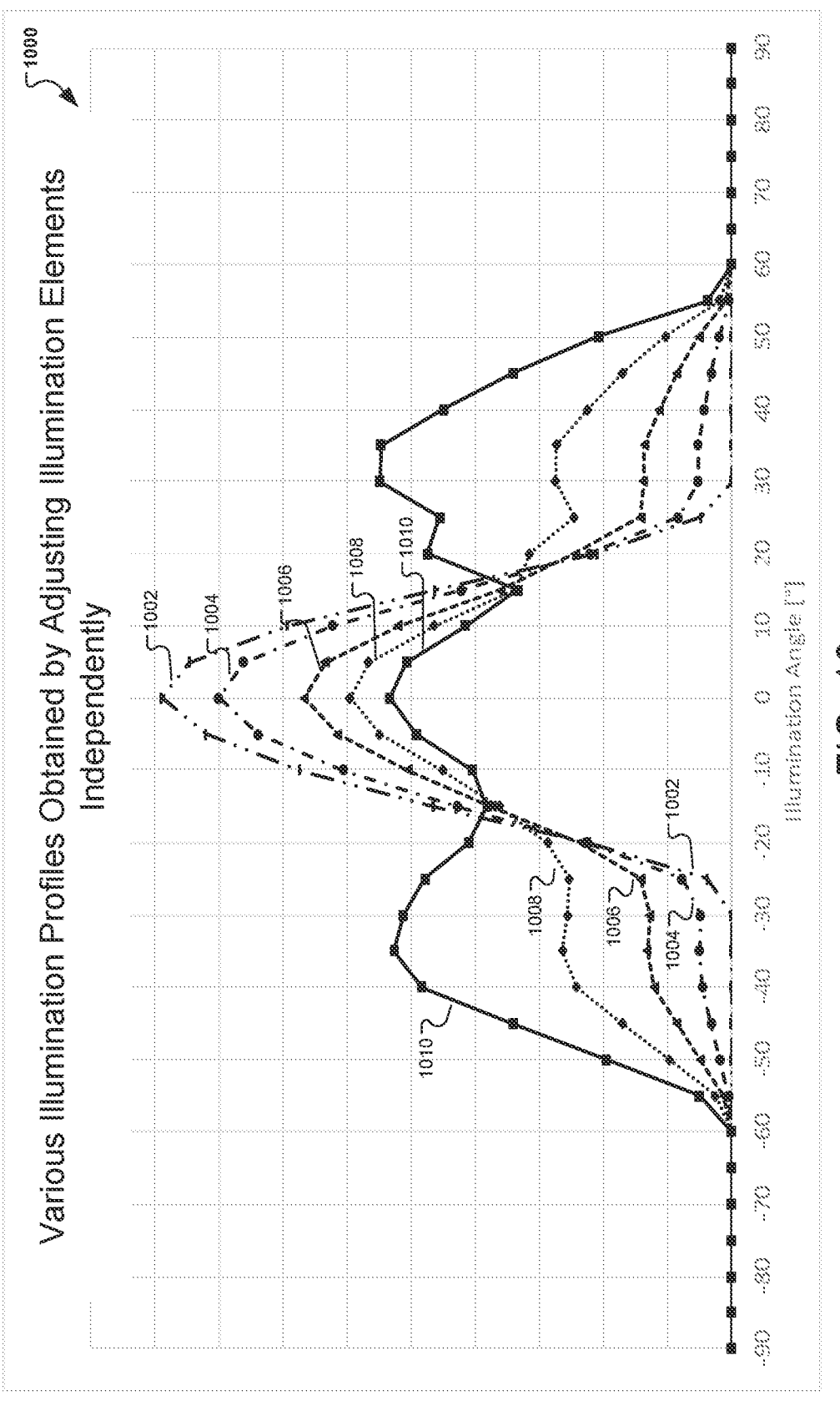
FIG. 10 shows a chart depicting a number of combined angular illumination profiles for an endoscopic illuminator according to some embodiments.

FIG. 10 shows a chart 1000 depicting a number of combined angular illumination profiles for an endoscopic illuminator according to some embodiments. Again, the vertical shows the illumination level, and the horizontal axis shows the angle of view as measured from directly perpendicular to the imaging lens or imager at the scope tip. The different profiles depict different combinations of illumination settings for the first and second illumination elements.

A first illumination profile 1002 results from a configuration in which the first or third illumination element is at its highest level illumination output, while the second or fourth illumination element is at its lowest level illumination output, i.e., turned off.

A second illumination profile 1004 results from a configuration in which the first or third illumination element has a high level illumination output, while the second or fourth illumination element has a low level illumination output.

A third illumination profile 1006 results from a configuration in which the first or third illumination element has a medium level illumination output, while the second or fourth illumination element has a medium level illumination output.

A fourth illumination profile 1008 results from a configuration in which the first or third illumination element has a medium level illumination output, while the second or fourth illumination element has a medium-high level illumination output.

A fifth illumination profile 1010 results from a configuration in which the first or third illumination element has a low level illumination output, while the second or fourth illumination element has a high level illumination output. This sort of uniform illumination profile is useful, for example, when an observed scene or an object of interest is flat or convex.

As can be understood, the particular number of profiles and number of illumination levels presented are merely examples, and a typical embodiment includes more levels of illumination available for each illumination element. In operation, an endoscopic illuminator such as endoscopic illuminator 105 of FIG. 2 may be used with an adaptive illumination control method like that of FIG. 8 to adjust between various illumination profiles, or, alternatively, the profiles may be adjusted manually for a specific illumination profile configuration desired and selected by a user. For example, in the process of FIG. 8, at block 808 the illumination profile in one example scenario might be illumination profile 1010 when the process enters block 808. This profile has a relatively high illumination level in the peripheral area of the field of view (corresponding to the side lobes of the illumination profile), and when the scope is oriented along a lumen, such a profile would typically have too much brightness in the periphery at block 808. As a result of the adjustment at block 810, the process may adjust the profile to be 1008 or 1006, through one or more adjustment steps.

Figure 11:
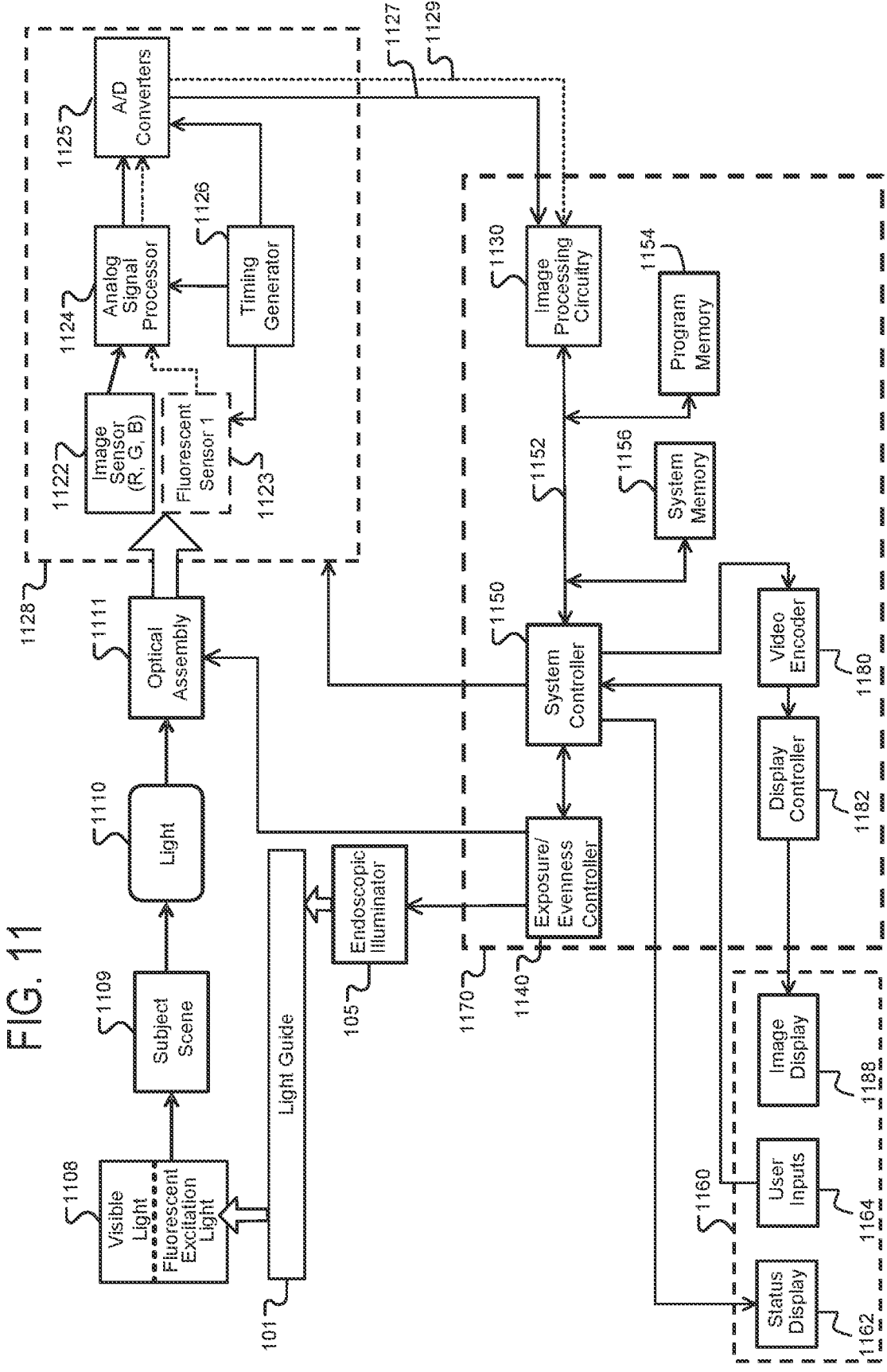
FIG. 11 shows a block diagram of an imaging system including an image capture device and an endoscope device having an improved endoscopic illuminator as described above.

FIG. 11 shows a block diagram of an imaging system including an image capture device and an endoscope device having an improved endoscopic illuminator as described above. The endoscopic illuminators disclosed herein are applicable to more than one type of device enabled for image capture, for example: endoscopes, borescopes, and other medical scopes.

As shown in FIG. 11, endoscopic illuminator 105 provides light to a light input of light guide 101, which is usually coupled to a light post of an endoscope, which in turn channels the light through the light guide of the endoscopic shaft to its distal end to illuminate the subject scene 1109 with illumination light. Endoscopic illuminator 105 may be implemented with any of the various embodiments shown herein, such as endoscopic illuminators 205, 305, and 405, as well as other suitable embodiments. As shown in the drawing, light 1110 reflected, scattered, or emitted from the subject scene is captured by an optical assembly 1111, where the light is focused to form an image at a solid-state image sensor(s) 1122 and/or fluoresced light sensor(s) 1123.

Figure 12:
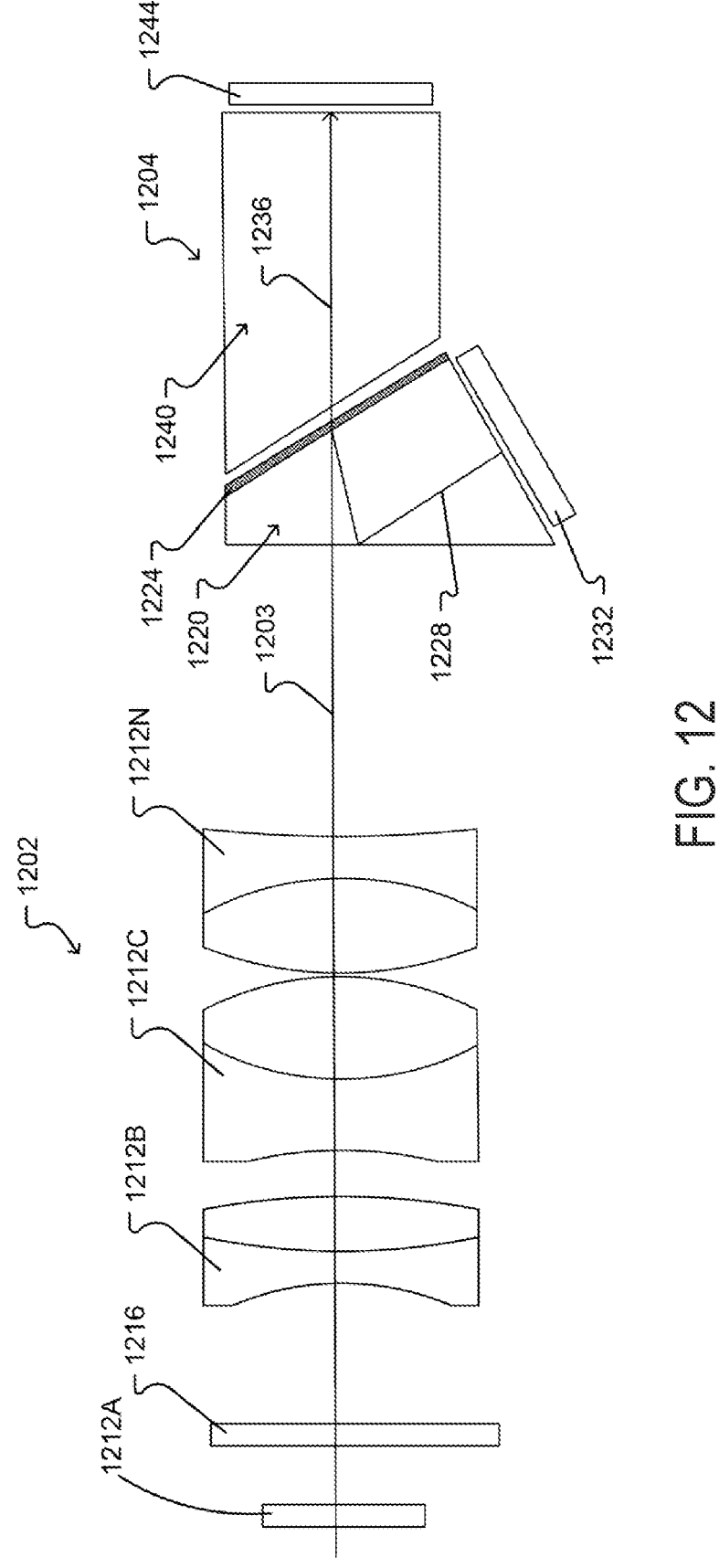
FIG. 12 is a diagram of an optical assembly including an image sensor assembly of an endoscopic camera head or video endoscope according to some embodiments.

Optical assembly 1111 generally includes one or more lenses and may include optical relay elements, including splitter elements for directing visible light and FI light to different image sensors. Portions of the optical assembly may be embodied in a camera head or other first optical device, while other portions are in an endoscope or other scope device, or the optical assembly 1111 may be contained in a single imaging device. Image sensor 1122 (which may include separate R, G, and B sensor arrays) and fluoresced light sensor 1123 convert the incident visible and invisible light to an electrical signal by integrating charge for each picture element (pixel). It is noted that fluoresced light sensor 1123 is shown as an optional dotted box because embodiments may use the RGB image sensor 1122 to detect only white light images or to also detect fluoresced light (e.g., NIR, ICG, FI). The latter scheme may be used when the fluoresced light is in a spectrum detectable by image sensor 1122 that is in or near the visible light spectrum typically detected by a RGB sensor arrays. In some embodiments, optical assembly 1111 may include a dichroic beam splitting element and may direct one band of the spectra to one sensor for visual imaging and another band to another sensor for fluorescence imaging, as shown in FIG. 12.

The image sensor 1122 and fluoresced light sensor 1123 may be active pixel complementary metal oxide semiconductor sensor (CMOS APS) or a charge-coupled device (CCD).

The total amount of light 1110 reaching the image sensor 1122 and/or fluoresced light sensor 1123 is regulated by the endoscopic illuminator 105 intensity, the optical assembly 1111 aperture, and the time for which each image sensor 1122 and fluoresced light sensor 1123 integrates charge.

An exposure/evenness controller 1140 performs an illumination profile control process such as that described with respect to FIG. 8, as well as controls exposure by responding to the amount of light available in the scene given the intensity and spatial distribution of digitized signals corresponding to the intensity and spatial distribution of the light focused on image sensor 1122. Exposure/evenness controller 1140 also controls the emission of fluorescent excitation light from endoscopic illuminator 105. Exposure/evenness controller 1140 may also control the optical assembly 1111 aperture, and indirectly, the time for which the image sensor 1122 integrate charges.

Typically, exposure/evenness controller 1140 has a different timing and exposure scheme for each of sensors 1122 and 1123. Due to the different types of sensed data, the exposure controller 1140 may control the integration time of the sensors 1122 and 1123 by integrating sensor 1122 up to the maximum allowed within a fixed 60 Hz or 50 Hz frame rate (standard frame rates for USA versus European video, respectively), while the fluoresced light sensor 1123 may be controlled to vary its integration time from a small fraction of sensor 1122 frame time to many multiples of sensor 1122 frame time. The frame rate of sensor 1122 will typically govern the synchronization process such that images frames based on sensor 1123 are repeated or interpolated to synchronize in time with the 50 or 60 fps rate of sensor 1122.

Analog signals from the image sensor 1122 and fluoresced light sensor 1123 are processed by analog signal processor 1124 and applied to analog-to-digital (A/D) converter 1125 for digitizing the analog sensor signals. The digitized signals each representing streams of images or image representations based on the data, are fed to image processor 1130 as image signal 1127, and first fluorescent light signal 1129. For versions in which the image sensor 1122 also functions to detect the fluoresced light, fluoresced light data is included in the image signal 1127, typically in one or more of the three color channels.

Image processing circuitry 1130 includes circuitry performing digital image processing functions to process and filter the received images as is known in the art. Image processing circuitry may include separate, parallel pipelines for processing the visible light image data and the FI image data separately. Such circuitry is known in the art and will not be further described here.

Image processing circuitry 1130 may provide algorithms, known in the art, for combining visible light imagery with FI imagery in a combined image display, and further highlighting or emphasizing the FI imagery for easily distinguishing the presence of fluorescing features in the image.

Timing generator 1126 produces various clocking signals to select rows and pixels and synchronizes the operation of image sensor 1122 and fluorescent sensor 1123, analog signal processor 1124, and A/D converter 1125. Image sensor assembly 1128 includes the image sensor 1122 and fluorescent sensor 1123, the analog signal processor 1124, the A/D converter 1125, and the timing generator 1126. The functional elements of the image sensor assembly 1128 can be fabricated as a single integrated circuit as is commonly done with CMOS image sensors or they can be separately-fabricated integrated circuits.

The system controller 1150 controls the overall operation of the image capture device based on a software program stored in program memory 1154. This memory can also be used to store user setting selections and other data to be preserved when the camera is turned off. The system controller 1150 may be in communication with the exposure/ evenness controller 1140 to provide desired adjustments to the optical assembly and/or the image sensors.

System controller 1150 controls the sequence of data capture by directing exposure controller 1140 to set the light intensity provided by the endoscopic illuminator 105, the optical assembly 1111 aperture, and controlling various filters in optical assembly 1111 and timing that may be necessary to obtain image streams based on the visible light and fluoresced light. In some versions, optical assembly 1111 includes an optical filter configured to attenuate excitation light and transmit the fluoresced light. A data bus 1152 includes a pathway for address, data, and control signals.

Processed image data are continuously sent to video encoder 1180 to produce a video signal. This signal is processed by display controller 1182 and presented on image display 1188. This display is typically a liquid crystal display backlit with light-emitting diodes (LED LCD), although other types of displays are used as well. The processed image data can also be stored in system memory 1156 or other internal or external memory device.

The user interface 1160, including all or any combination of image display 1188, user inputs 1164, and status display 1162, is controlled by a combination of software programs executed on system controller 1150. The user inputs typically include some combination of typing keyboards, computer pointing devices, buttons, rocker switches, joysticks, rotary dials, or touch screens. The system controller 1150 manages the graphical user interface (GUI) presented on one or more of the displays (e.g. on image display 1188). In particular, the system controller 1150 will typically have a mode toggle user input (typically through a button on the endoscope or camera head itself, but possibly through a GUI interface), and in response transmit commands to adjust image processing circuitry 1130 based on predetermined setting stored in system memory. Preferably a system employed with any of the device designs herein provides ability to toggle between at least two modes, visible light and FI modes, and more preferably a combined mode is included in which FI images are combined or overlaid with visible images in a suitable manner known in the art. Such settings may include different settings for different models of scopes that may be attached to a camera head or other imaging device containing image sensor assembly 1128.

Image processing circuitry 1130 is one of three programmable logic devices, processors, or controllers in this embodiment, in addition to a system controller 1150 and the exposure controller 1140. Image processing circuitry 1130, controller 1150, exposure controller 1140, system and program memories 1156 and 1154, video encoder 1180 and display controller 1182 may be housed within camera control unit (CCU) 1170.

CCU 1170 may be responsible for powering and controlling endoscopic illuminator 105, image sensor assembly 1128, and/or optical assembly 1111. In some versions, a separate front end camera module may perform some of the image processing functions of image processing circuitry 1130.

Although this distribution of imaging device functional control among multiple programmable logic devices, processors, and controllers is typical, these programmable logic devices, processors, or controllers can be combinable in various ways without affecting the functional operation of the imaging device and the application of the invention. These programmable logic devices, processors, or controllers can comprise one or more programmable logic devices, digital signal processor devices, microcontrollers, or other digital logic circuits. Although a combination of such programmable logic devices, processors, or controllers has been described, it should be apparent that one programmable logic device, digital signal processor, microcontroller, or other digital logic circuit can be designated to perform all of the needed functions. All of these variations can perform the same function and fall within the scope of this invention.

FIG. 12 is a diagram of an optical assembly and an imaging assembly that may be elements of a camera head 30 or other endoscopic/exoscopic device that may be used in conjunction with the embodiments of the endoscopic illuminator described herein. For clarity, the optical/imaging assemblies of FIG. 12 will be described with respect to a camera head 30 that may be attached to an endoscope 10, however it should be appreciated by those skilled in the art that the following description is not limited to being housed within a camera head, but may alternatively be elements of a video endoscope, exoscope, microscope, etc.

The camera head 30 includes a lens assembly 1202 and an imaging assembly 1200 including a prism assembly 1204. The lens assembly 1202 may include a collection of mirrors, lenses, filters, polarizers, and/or windows capable of conditioning and directing received light into the prism assembly 1204. As shown in FIG. 12, the lens assembly 1202 includes a plurality of lenses 1212A-1212N and a first filter 1216, which may channel the light 1203 to the prism assembly 1204. In some embodiments, the light 1203 may be light reflected, scattered, or emitted from a surgical scene and captured by the optics of an attached endoscope or those of an exoscope and be relayed or transmitted to the camera head 30. The first filter 1216 may filter out one or more wavelengths of the light captured by the camera head 30. The first filter 1216 may be a replaceable, selectable, or tunable filter, such that its characteristics may be selected depending on the requirements of the desired mode. For example, in one embodiment the first filter 1216 may be a dichroic filter that passes light in a first wavelength band but rejects light in a second wavelength band. In a further embodiment, the first filter 1216 may be a different dichroic filter that passes light from a third wavelength band and rejects light from a fourth wavelength band. Various particular implementations are discussed below. In an example embodiment, the first filter 1216 blocks wavelengths between 725 nm and 800 nm. The first filter 1216 may be removable from the lens assembly 1202. The first filter 1216 may be used in FI imaging modalities to block illumination wavelengths that are used to stimulate the fluorescence but would be deleterious if detected by the image sensors, such as when the excitation and emission wavelengths of a given fluorophore partially overlap. While some wavelengths are filtered out by the first filter 1216, the transmitted light may nonetheless contain additional spectrally distinct portions of light. For example, the transmitted light may include fluorescence wavelengths as well as visible light wavelengths, which may be individually separated by the prism assembly 1204 as discussed in further detail below.

The light 1203 is focused by the lens assembly 1202 and passes into the prism assembly 1204. The prism assembly 1204 includes a first prism 1220 that receives the light 1203. The first prism 1220 may include a first spectral filter 1224 disposed on a surface thereof. The first spectral filter 1224 may filter and reflect different wavelengths of light, creating a cutoff between different spectral bands. For example, the first spectral filter 1224 may reflect light with wavelengths in the NIR band while transmitting light with wavelengths in the visible light band. As a result, the spectral band with wavelengths in the visible band pass out of the first prism 1220 as transmitted light 1236, while the remaining spectral bands remain in the first prism 1220 as reflected light 1228. The reflected light 1228 may be bent by or reflected inside the first prism 1220 until the reflected light 1228 passes into a first image sensor 1232. The first image sensor 1232 may receive the reflected light 1228 and photosensitive elements (e.g., photodiodes, pixels) within the first image sensor 1232 generate corresponding electric signals. The electric signals may be passed to one or more other components of the system as described with respect to FIG. 11.

Transmitted light 1236 may pass through the first spectral filter 1224 and may enter a second prism 1240. The second prism 1240 may include a second image sensor 1244. The second image sensor 1244 may be similar to or the same as the first image sensor 1232 or, in more preferred embodiments may be a sensor specifically designed for the detection of white light, such a sensor with an integrated Bayer filter for the separation of light into distinct red, blue, and green channels, as is known in the art.

In some embodiments, the first image sensor 1232 and/or the second image sensor 1244 may be respectively attached (e.g., glued or adhered to) the first prism 1220 and the second prism 1240. Alternatively, the first image sensor 1232 and/or the second image sensor 1244 may not be respectively attached to the first prism 1220 and the second prism 1240 and may instead be disposed proximate the first prism 1220 and the second prism 1240. In such embodiments, the position of the first image sensor 1232 and/or the second image sensor 1244 relative to the first prism 1220 and/or the second image sensor 1244 may be able to be adjusted or changed.

In this manner the optical system shown in FIG. 12 may be used in conjunction with the various embodiments of the endoscopic illuminator 105, 205, 305, 405 disclosed herein, when used as an element of an endoscope, video endoscope, video exoscope, or camera head attached to an endoscope, exoscope, or microscope, to enable simultaneous collection of FI and visible light images. FI light is passed to the FI sensor 1232 and white light is passed to the visible light sensor 1244, and the respective sensors generate image signals therefrom. Image processing circuitry 1130 can then combine the resultant images such that a false colored FI image can be overlaid on the white light image and displayed on the image display 1188. Alternatively, the optical system presented in FIG. 12 or other optical systems may be employed to operate in distinct FI or visible light modes or may be used to detect FI and visible light sequentially, as described above.

As used herein the terms "comprising," "including," "carrying," "having" "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The foregoing has outlined rather broadly the features and technical advantages of the invention in order that the detailed description of the invention that follows may be better understood. It should be appreciated by those skilled in the art that the conception and specific embodiments disclosed may be readily utilized as a basis for modifying or designing other structures for carrying out the same purposes of the invention. It should also be realized by those skilled in the art that such equivalent constructions do not depart from the scope of the invention as set forth in the appended claims.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manu-facture, compositions of matter, means, methods, or steps, presently existing or later to be developed that perform substantially the same function or achieve substantially the same result as the corresponding embodiments described herein may be utilized according to the invention. Accord-ingly, the appended claims are intended to include within their scope such processes, machines, manufacture, compo-sitions of matter, means, methods, or steps.

The invention claimed is:

1. An endoscopic illuminator comprising:
a first illumination element adapted for coupling first illumination light into a light input of an endoscope for illuminating a central area of a field of view of the endoscope;
a second illumination element adapted for coupling sec-ond illumination light to the light input for illuminating a peripheral area of the field of view, arranged relative to the first illumination element such that the first illumination light enters the light input at a substan-tially different angle from the first second illumination light, and having an illumination level adjustable sepa-rately from that of the first illumination element;
a third illumination element adapted for coupling third illumination light, of a different spectral band than that of the first and second illumination light, into the light input for illuminating the central area; and
a fourth illumination element adapted for coupling fourth illumination light, of the same spectral band as the third illumination light, to the light input for illuminating the peripheral area, arranged relative to the third illumina-tion element such that the fourth illumination light enters the light input at a substantially different angle from the third illumination light, and having an illumi-nation level adjustable separately from that of the third illumination element.

2. The endoscopic illuminator of claim 1, wherein the first and second illumination elements provide white light to the endoscopic field of view and the third and fourth illumina-tion elements provide illumination to excite fluorescence in the endoscopic field of view.

3. The endoscopic illuminator of claim 2, wherein the third and fourth illumination elements provide illumination at wavelength between 750 and 800 nm for stimulating Indocyanine green (ICG) or near infrared (NIR) fluores-cence.

4. The endoscopic illuminator of claim 1 wherein the illumination elements each comprise a light source and a light directing element arranged for directing light from the light source to the light input at their respective different angles.

5. The endoscopic illuminator of claim 4 wherein the light directing elements comprise lenses.

6. The endoscopic illuminator of claim 1, wherein at least one of the light directing elements comprises a parabolically shaped dichroic beam combiner.

7. The endoscopic illuminator of claim 4, wherein at least one of the light directing elements comprises a dichroic beam combiner.

8. The endoscopic illuminator of claim 1 wherein the illumination elements are adapted to couple light into the light input, and the light input is selected from the group comprising: an input of a light post of the endoscope, a light port of the endoscope, an input of a light cable of the endoscope, an input of a light pipe of the endoscope, and an optical element for coupling to an endoscopic light input.

9. The endoscopic illuminator of claim 1 further compris-ing a controller coupled to the illumination elements and operable in a first mode to automatically adjust the illumi-nation levels of the first and second illumination elements to improve the evenness of illumination over a field of view of the endoscope, and operable in a second mode to automati-cally adjust the illumination levels of the third and fourth illumination elements to improve the evenness of illumina-tion over a field of view of the endoscope.

10. The endoscopic illuminator of claim 9 wherein, in the first and second modes, the illumination at the edges of the endoscopic field of view is automatically decreased relative to the illumination at the center of the field of view when the endoscope images along a lumen, and wherein the illumi-nation at the edges of the endoscopic field of view is automatically increased relative to the illumination at the center of the field of view when the endoscope images a flat or convex scene.

11. The endoscopic illuminator of claim 1 wherein an optical axis of at least one illumination element providing illumination to the center of the endoscopic field of view is oriented at an angle more than 0° and less than 5° with respect to a longitudinal axis of the light input into which the illumination is coupled.

12. A method of providing illumination for an endoscope, comprising:
coupling first illumination light into a proximal end of a light guiding element for an endoscope centered along a first angle relative to the light guiding element;
illuminating a central area of a field of view of the endoscope from a distal end of the light guiding ele-ment with the first illumination light;
while coupling the first illumination light, coupling sec-ond illumination light into the light guiding element centered along a second angle substantially different from the first angle;
illuminating a peripheral area of the field of view with the second illumination light;
adjusting an illumination level of the second illumination light relative to that of the first illumination light to improve evenness of illumination in the field of view;
coupling third illumination light, of a different spectral band than that of the first and second illumination light, into the proximal end of the light guiding element centered along the first angle;
illuminating a central area of a field of view of the endoscope from the distal end of the light guiding element with the third illumination light;
while coupling the third illumination light, coupling fourth illumination light into the light guiding element centered along a substantially different angle than the first angle;
illuminating a peripheral area of the field of view with the fourth illumination light; and
adjusting an illumination level of the fourth illumination light relative to that of the third illumination light to improve evenness of illumination in the field of view.

13. The method of claim 12, further comprising:

detecting a first illumination level in the central area of the field of view and detecting a second illumination level in the peripheral area of the field of view; and based on the first and second illumination levels, automatically adjusting the illumination level of the third or fourth illumination light.

14. The method of claim 12, further wherein:

coupling third illumination light into the proximal end of the light guiding element comprises directing the third illumination light at a light guide element comprising a dichroic beam combiner.

15. An endoscopic imaging system comprising:

an endoscope comprising a shaft, a light guide extending along at least a portion of the shaft to a distal end of the shaft, and a light input;

a light source comprising:

a first illumination element providing first illumination light into the light input, which is emitted by the light guide to illuminate a central area of a field of view of the endoscope;

a second illumination element providing second illumination light to the light input and arranged relative to the first illumination element such that the second illumination light enters the light input at a substantially different angle from the first illumination light, which is emitted by the light guide to illuminate a peripheral area of the field of view, the second illumination element having an illumination level adjustable separately from that of the first illumination element;

a third illumination element providing third illumination light, of a different spectral band than that of the first and second illumination light, into the light input, the third illumination light emitted by the light guide to illuminate a central area of a field of view of the endoscope; and a fourth illumination element providing fourth illumination light of the same spectral band as the third illumination light to the light input and arranged relative to the third illumination element such that the fourth illumination light enters the light input at a substantially different angle from the third illumination light and is emitted by the light guide to illuminate a peripheral area of the field of view, the fourth illumination element having an illumination level adjustable separately from that of the third illumination element.

16. The endoscopic imaging system of claim 15, further comprising a controller coupled to the first and second illumination elements and operable in a first mode to adjust at least one of the first and second illumination elements to improve the evenness of illumination over an endoscopic field of view, and operable in a second mode to adjust at least one of the third and fourth illumination elements to improve the evenness of illumination over the endoscopic field of view.

17. The endoscopic imaging system of claim 15, wherein the first and second illumination elements provide white light to the endoscopic field of view and the third and fourth illumination elements provide illumination to excite fluorescence in the endoscopic field of view.

18. The endoscopic imaging system of claim 17, wherein the third and fourth illumination elements provide illumination at wavelength between 750 and 800 nm for stimulating Indocyanine green (ICG) or near infrared (NIR) fluorescence.

19. The endoscopic imaging system of claim 15 wherein the third and fourth illumination elements each comprise a light source and a light directing element arranged for directing the illumination from the light source to the light input at their respective different angles.

20. The endoscopic imaging system of claim 19, wherein at least one of the light directing elements comprises a dichroic beam combiner.

* * * * *